United States Patent [19]

Sawada et al.

[11] Patent Number: 4,914,205
[45] Date of Patent: Apr. 3, 1990

[54] CAMPTOTHECIN DERIVATIVES

[75] Inventors: Seigo Sawada; Kenichiro Nokata; Satoru Okajima; Hisako Nagai; Takashi Yaegashi; Kenichi Tezuka, all of Tokyo; Tadashi Miyasaka, Kanagawa, all of Japan

[73] Assignee: Kabushiki Kaisha Yakult Honsha, Tokyo, Japan

[21] Appl. No.: 210,918

[22] Filed: Jun. 24, 1988

[30] Foreign Application Priority Data

Jun. 25, 1987 [JP] Japan .................. 62-156495

[51] Int. Cl.$^4$ ........................... C07D 487/12
[52] U.S. Cl. ........................ 546/70; 546/48
[58] Field of Search ................ 546/70, 48

[56] References Cited

U.S. PATENT DOCUMENTS

Re. 32,518 10/1987 Miyasaka et al. ............ 546/48
4,031,098 6/1977 Sugasawa ..................... 546/70

FOREIGN PATENT DOCUMENTS 2534601 2/1977 Fed. Rep. of Germany ........ 546/48

OTHER PUBLICATIONS

Gottlieb et al., Cancer Chemother. Reports, Part 1, vol. 54, No. 6, pp. 461–470 (1970).
Cai et al., the Alkaloids, vol. 21, Chapter 4 (Academic Press, Inc.) pp. 101–137 (1983).
Wani et al., J. Med. Chem., vol. 23, No. 5, pp. 594–560 (1980).
Adanovics et al., J. Med. Chem., vol. 22, No. 3, pp. 310–314 (1979).
Sugasawa et al., J. Med. Chem., vol. 19, No. 5, pp. 675–679 (1976).

Primary Examiner—Mukund J. Shah
Assistant Examiner—Andrew G. Rozycki

[57] ABSTRACT

New camptothecin derivatives, useful as antitumor agents or intermediates therefor, of the general formula (I)

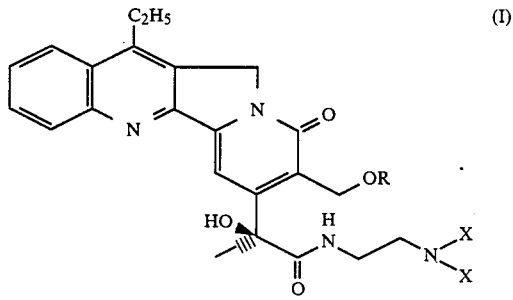

wherein
X is a lower alkyl group, and R is a hydrogen atom or the grouping -COY where Y is a linear or branched unsubstituted $C_1$–$C_{18}$ alkyl group; a lower alkyl group substituted by a halogen atom or a lower alkylthio, amino, acylamino, hydroxyl, lower alkoxy, aryloxy or lower alkoxycarbonyl group; a $C_3$–$C_{19}$ alkenyl, $C_3$–$C_{19}$ alkynyl or $C_3$–$C_8$ cycloalkyl group; a $C_3$–$C_8$ cycloalkyl group substituted by an acylamino-lower alkyl group; an N-acylpyrrolidyl group; a phenyl group; a phenyl group substituted by a halogen atom or a trifluoromethyl, nitro, amino, lower alkoxycarbonyl, lower alkyl, phenyl or lower alkoxy; a cinnamyl group; a benzyl group; a naphthyl group; a pyridyl group; a furyl group; or a thienyl group, as well as acid addition salts and quaternary ammonium salts thereof, and a process for preparing the new camptothecin derivatives by subjecting 7-ethylcamptothecin to the treatment with an N-di-X-ethylenediamine followed by acylation.

1 Claim, No Drawings

CAMPTOTHECIN DERIVATIVES

BACKGROUND OF THE INVENTION

1. Field of the Invention

The present invention relates to new camptothecin derivatives useful as anti-tumor agents or intermediates thereof and to a process for preparing such derivatives. More particularly, the present invention relates to new prodrug-type camptothecin derivatives which exhibit excellent anti-tumor activity in living body with a low level of toxicity as well as a process for the preparation of the new camptothecin derivatives starting from 7-ethylcamptothecin.

2. Description of the Prior Art

Camptothecin is an alkaloid extracted and isolated from Camptotheca acuminata (Nyssaceae), etc., which has a pentacyclic structure consisting of a characteristic fused 5-ring system consisting of quinoline (rings A and B), pyrroline (ring C), α-pyridone (ring D) and a six-membered lactone (ring E) and is distinguished by displaying a strong inhibitory activity toward biosynthesis of nucleic acid. In addition, camptothecin is a unique anti-tumor substance characterized by its rapid and reversible action and its lack of any cross-tolerance with the existing anti-tumor agents and by exhibiting a strong anti-tumor activity against experimentally transplanted carcinoma such as leukemia L-1210 in mice or Walker 256 sarcoma in rats. Although camptothecin is still regarded as one of the most potent substances possessing anti-tumor activity, the use of this compound itself for clinical treatments is significantly limited because of its high toxicity. Moreover, camptothecin and the majority of derivatives thereof are sparingly soluble in water and thus involve a problem in case of administration as medicaments.

Accordingly, a number of attempts have been made not only to reduce toxicity of camptothecin while maintaining its anti-tumor activity by converting camptothecin chemically into its derivatives but also to make camptothecin and derivatives thereof easily soluble in water by chemical modifications of the camptothecin molecule or substituents therein. As one of such attempts, 10-hydroxy-substituted derivatives among the camptothecin derivatives having been prepared hitherto provided interesting results in that the 10-hydroxy-substituted derivatives maintain an excellent anti-tumor activity with reduced toxicity. However, the derivatives were found to be sparingly soluble in water and therefore cannot be used as a medicament without difficulty. As a method for making camptothecin derivatives soluble in water, for example, a ring-opening reaction for the E-ring (lactone ring) of the camptothecin derivatives was used in the prior arts to form an alkali metal salt of the carboxyl function. However, a result of any chemical modification of the ring E, including such ring-opening reaction, revealed only failure in maintaining anti-tumor activity and very poor improvement in toxicity [J. Med. Chem., 19 (1976), 675].

According to a prior report, a water-soluble derivative of camptothecin of the formula (II) (hereinafter referred to as camptothecin sodium salt) obtainable by the treatment of the E-ring (the lactone moiety) of camptothecin with an aqueous sodium hydroxide solution is not found to be useful as anti-tumor agent because of its toxicity of causing e.g. myelosuppression or hemorrhagic cystitis constituting a dose limiting factor [Cancer Chemother. Rep., 54, 461 (1970)].

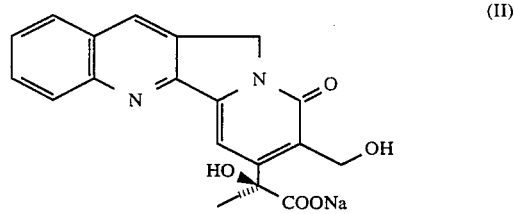

(II)

M. C. Wani et al, reported that the anti-tumor activity of the camptothecin sodium salt is reduced to a fraction of what is found in a derivative with the lactone form [M. C. Wani et al., J. Med. Chem., 23, 554 (1980)]. It has been believed since then that the E-ring (the lactone moiety) of camptothecin, including the 20-hydroxyl group, is an essential partial structure for camptothecin to exhibit its anti-tumor activity. Any of the few previous reports on the chemical modification of the E-ring (the lactone moiety) revealed that the derivatives obtained by such chemical modification exhibit only a little or no anti-tumor activity. For example, an E-ring (lactone)-opened derivative as the methylamide of the formula (III) shown below or as the isopropylamide of the formula (IV) shown below was reported to show a very little or no activity [The Alkaloids, ed. by A. Brossi, Academic Press, N.Y., 1983 and J. Med. Chem., 22, 310 (1979)].

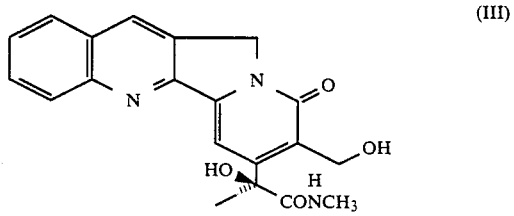

(III)

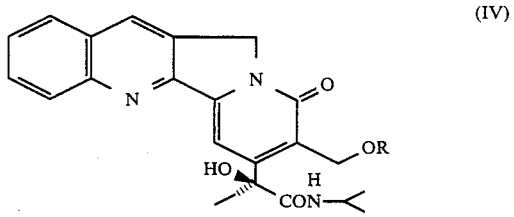

(IV)

(wherein R is H, acetyl or propionyl.)

From the studies on various camptothecin derivatives prepared heretofore, it now becomes evident that chemical modifications in the E-ring, especially the E-ring opening of camptothecin derivatives significantly adversely affect the anti-tumor activity. Under the circumstances, there is a great demand in this art for developing a new class of camptothecin derivatives maintaining strong anti-tumor activity even if chemically modified in the E-ring.

As a part of our studies on the preparation of water-soluble prodrug-type derivatives of camptothecin, we fixed our eyes on the E-ring of camptothecin derivatives to explore the possibility of converting them into a prodrug form. As the 17-hydroxy group of camptothecin in free form is spontaneously cyclized under a neutral condition with the partner carboxyl group to form a lactone ring, we have made extensive researches to solve simultaneously both problems of making the derivatives water-soluble and reconstructing the E-ring of the E-ring-opened derivatives in living body after administration by masking the 17-hydroxy group of the E-ring-opened derivatives with such a protecting group as will be split off by hydrolysis by the action of an endogenous enzyme and converting the partner carboxyl group into a water-soluble carboxamide group.

BRIEF SUMMARY OF THE INVENTION

Accordingly, it is an object of the present invention to provide new prodrug-type camptothecin derivatives which exhibit excellent anti-tumor activity with a low level of toxicity.

It is another object of the present invention to provide new E-ring-opened camptothecin derivatives which are convertible into derivatives with the E-ring in the living body.

It is still another object of the present invention to provide a process for preparing water-soluble E-ring-opened camptothecin derivatives starting from 7-ethyl-camptothecin.

Other objects, features and advantages of the present invention will become apparent more fully from the following description.

As a result of our extensive researches made for developing new water-soluble camptothecin derivatives to achieve the above mentioned objects, we have succeeded in opening the E-ring of 7-ethylcamptothecin with an N,N-dialkylethylenediamine to obtain E-ring-opened carboxamide derivatives which can easily be converted in the living body into the derivatives having the corresponding E-ring.

In accordance with one embodiment of the present invention there is provided new camptothecin derivatives of the general formula:

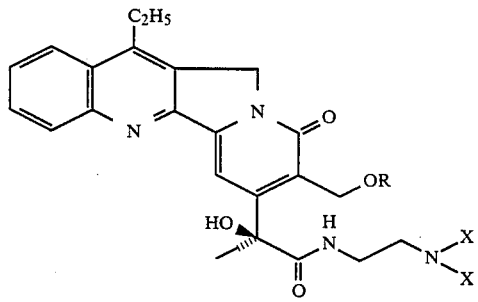
(I)

wherein X is a lower alkyl group, and R is a hydrogen atom or the grouping -COY where Y is a linear or branched unsubstituted $C_1$–$C_{18}$ alkyl group; a lower alkyl group substituted by a halogen atom or a lower alkylthio, amino, acylamino, hydroxyl, lower alkoxy, aryloxy or lower alkoxycarbonyl group; a $C_3$–$C_{19}$ alkenyl, $C_3$–$C_{19}$ alkynyl or $C_3$–$C_8$ cycloalkyl group; a $C_3$–$C_8$ cycloalkyl group substituted by an acylamino-lower alkyl group; an N-acylpyrrolidyl group; a phenyl group; a phenyl group substituted by a halogen atom or a trifluoromethyl, nitro, amino, lower alkoxycarbonyl, lower alkyl, phenyl or lower alkoxy; a cinnamyl group; a benzyl group; a naphthyl group; a pyridyl group; a furyl group; or a thienyl group, and their acid addition salts formed at the amino group and quaternary ammonium salts.

In accordance with another embodiment of the present invention, there is provided a process for the preparation of new camptothecin derivatives of the general formula:

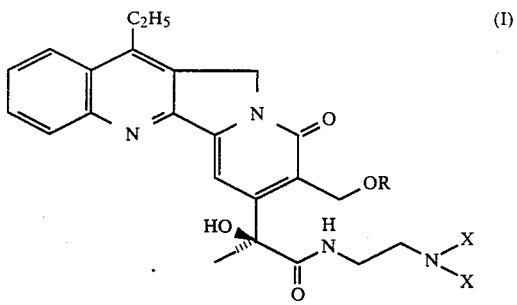
(I)

wherein X is a lower alkyl group, and R is a hydrogen atom or the grouping -COY where Y is a linear or branched unsubstituted $C_1$–$C_{18}$ alkyl group; a lower alkyl group substituted by a halogen atom or a lower alkylthio, amino, acylamino, hydroxyl, lower alkoxy, aryloxy or lower alkoxycarbonyl group; a $C_3$–$C_{19}$ alkenyl, $C_3$–$C_{19}$ alkynyl or $C_3$–$C_8$ cycloalkyl group; a $C_3$–$C_8$ cycloalkyl group substituted by an acylamino-lower alkyl group; an N-acylpyrrolidyl group; a phenyl group; a phenyl group substituted by a halogen atom or a trifluoromethyl, nitro, amino, lower alkoxycarbonyl, lower alkyl, phenyl or lower alkoxy; a cinnamyl group; a benzyl group; a naphthyl group; a pyridyl group; a furyl group; or a thienyl group, and their physiologically acceptable acid-addition salts at the amino group, which comprises treating 7-ethylcamptothecin with an ethylenediamine derivative of the general formula:

$H_2N\text{-}CH_2CH_2\text{-}NX_2$ (VI)

wherein X has the same meaning as given above, to form a 7-ethyl-17-hydroxymethylcamptothecin-21-(2-dialkylamino)ethylamide of the general formula:

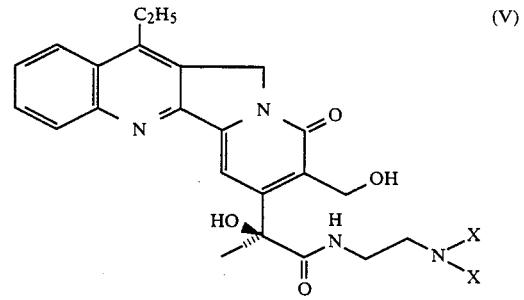
(V)

wherein X has the same meaning as given above, and if necessary, acylating the resultant compound of the general formula (V) with a compound of the general formula

Z-COY (VII)

wherein Y has the same meaning as given above and Z is a hydroxyl group, a halogen atom or the grouping -O-COY, and if desired, converting the resultant compound of the general formula (I) into its physiologically acceptable acid addition salt or quaternary ammonium salt or vice versa.

In the general formula (I) standing for the new compounds of this invention, the lower alkyl, alkoxy and alkylthio groups have 1–6, preferably 1–4 carbon atoms in the alkyl moiety. Thus, the term "lower" is to be interpreted as having 1–6 carbon atoms. These groups may be linear or branched in their alkyl moiety. Illustrative of the lower alkyl group and the linear or branched unsubstituted $C_1$–$C_{18}$ carbon atoms are, for example, methyl, ethyl, n-propyl, isopropyl, n-butyl, iso-butyl, tert-butyl, pentyl, hexyl, heptyl, octyl, nonyl, decyl, undecyl, dodecyl, tetradecyl, hexadecyl and octadecyl. Examples of the lower alkoxy group include methoxy, ethoxy, n-propoxy, isopropoxy, n-butoxy, pentoxy, hexoxy. Examples of the lower alkylthio include alkylthio groups corresponding to the aforesaid alkoxy groups. Examples of the alkenyl groups with 1–19 carbon atoms include propenyl, butenyl, pentenyl, hexenyl, heptenyl, octenyl, nonenyl, decenyl, undecenyl, dodecenyl, tetradecenyl, hexadecenyl, octadecenyl and nonadecenyl groups. Mentioned as the alkynyl group with 1–19 carbon atoms are alkynyl groups corresponding to the aforesaid alkenyl groups. The acyl moiety in the acylamino and N-acylpyrrolidyl groups stands for a residue of an acid preferably selected from aliphatic and aromatic carboxylic acids including amino acids, aliphatic and aromatic sulfonic acids, and halogen- or hydroxy-substituted derivatives thereof.

In case the acyl group is derived from an amino acid, it may contain a protective group for the amino group. A preferable acyl moiety is, for example, a lower alkanoyl or benzoyl group which may be substituted. The aryl moiety of the aryloxy group is selected from phenyl and naphthyl.

Illustrative of the cycloalkyl group are, for example, cyclopropyl, cyclopentyl, cyclohexyl, cycloheptyl and cyclooctyl groups, with cyclopropyl, cyclopentyl and cyclohexyl being preferable.

7-ethylcamptothecin used as the main starting material is commercially available or can be prepared according to the process disclosed in U.S. Pat. Re. No. 32,518.

Preferable examples of the N,N-di(lower alkyl)-ethylenediamine used for opening the E-ring of 7-ethylcamptothecin include N,N-dimethyl-ethylenediamine, N,N-diethyl-ethylenediamine, N,N-dipropyl-ethylenediamine and N,N-dibutyl-ethylenediamine.

The process of this invention for preparing the new camptothecin derivatives comprises the two steps of treating 7-ethylcamptothecin with an N,N-di(lower alkyl)-ethylenediamine and optionally acylating the 17-hydroxyl group of the resultant compound with a compound of the general formula:

Z-COY (VII)

wherein Y and Z have the same meanings as given above, to obtain a compound of the general formula:

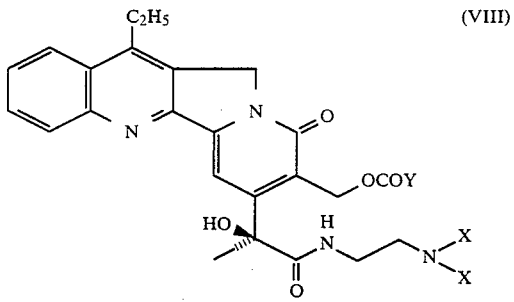

wherein X, Y and Z have the same meanings as given above.

In the first step for the treatment with an N,N-di(lower alkyl)-ethylenediamine, 7-ethylcamptothecin is dissolved in an excess amount of the N,N-di(lower alkyl)-ethylenediamine. As an excess amount of the N,N-di(lower alkyl)-ethylenediamine functions as a reaction solvent, there is generally no necessity of using a reaction solvent additionally. The solution was then stirred preferably in a nitrogen atmosphere for a period generally from 10 minutes to 5 hours, preferably from 30 minutes to 2 hours within the temperature range from room temperature to 100° C., preferably at 30°–70° C. By raising the reaction temperature, the reaction time may be shortened accordingly. After completion of the reaction, the excess N,N-di(lower alkyl)-ethylenediamine is distilled off under reduced pressure. The residue is taken up in a solvent such as methylene chloride or chloroform and the solution is added to an inert solvent such as n-hexane in an amount of several times as much as the solution whereby the resultant compound is precipitated as crystals which are then collected by filtration. 7-Ethyl-17-hydroxycamptothecin-21-[2-di(lower alkyl)]amino ethylamide as an E-ring-opened product is thus obtained in a theoretical yield. This compound can be shown by the general formula (V) and can optionally be acylated in the 17-hydroxyl position thereof. This compound reverts to the starting compound 7-ethylcamptothecin, when allowed to stand in a solution thereof or subjected to column chromatography on silica gel.

In the subsequent step for the optional acylation, the reaction itself is carried out according to a usual manner for acylation of the hydroxyl group. The E-ring-opened camptothecin derivative of the general formula (V) is dissolved in a solvent and a catalytic amount of 4-N,N-dimethylaminopyridine is added to the solution. Illustrative of the solvent used for this acylation are, for example, methylene chloride, chloroform, DMF, dimethylsulfoxide and ether. The solution is stirred under cooling, preferably under ice-cooling and a compound of the general formula (VII) as acylating agent alone or in a solvent as above mentioned is added, and the mixture is continuously stirred under cooling or at room temperature until the reaction is completed. Water is then added to the reaction mixture and then an aqueous solution of caustic alkali, for example, 1N-NaOH solution is added to the mixture to make it weakly alkaline. The resultant compound is extracted with methylene chloride or chloroform and the extract is washed with a saturated aqueous solution of edible salt. The organic phase is then dried over magnesium sulfate or sodium sulfate and then concentrated under reduced pressure until dryness. The residue is then subjected to column chromatography on silica gel whereby a 17-acylated compound of the general formula (VIII) is obtained in a moderate yield.

Alternatively, the 17-acylated compound can be obtained by treating a compound of the general formula (VII) with a condensing agent such as dicyclohexylcarbodiimide or the like mild dehydrating agent and then reacted with the E-ring-opened compound of the general formula (V) in the presence of N,N-dimethylaminopyridine, and can be purified in the same manner as described above.

The compounds of this invention represented by the general formula (I) can be converted, if desired, into a physiologically acceptable acid addition salts or quaternary salts thereof with proper inorganic or organic acids or alkyl or aryl halides, respectively. Examples of the inorganic and organic acids used for the preparation of acid addition salts include hydrohalic acids such as hydrochloric acid, sulfuric acid, methanesulfonic acid, alkanoic acids such as acetic acid, and alkanedicarboxylic acids such as tartaric acid, citric acid, etc. Preferable examples of the alkyl halide include methyl iodide and ethyl bromide. In order to prepare these salts, the compound of the general formula (I) is incorporated with the acid or the alkyl halide in an equimolar amount and then the mixture is heated until dryness or lyophilized. The acid addition salts can be liberated by the treatment with an alkaline substance.

The acid addition salts are formed at the amino group of the ethylenediamine moiety and the quaternary salts are formed at the tertiary amino group.

The new camptothecin derivatives of this invention are useful as medicaments or intermediates therefore. A recommended dose of the derivatives is generally 1–400 mg/kg of body weight in case of a rat.

The present invention will now be illustrated in more detail by way of examples. It is to be construed, however, that the scope of this invention is not limited by these examples.

EXAMPLE 1

(Preparation of 7-ethyl-17-hydroxycamptothecin-21-(2-dimethylamino)-ethylamide)

7-Ethylcamptotecin(1.00 g, 2.66 mmol) was stirred in N,N-dimethylethylenediamine(20 ml) for an hour at 50° C. under the $N_2$ atmosphere. After the stirring, the reaction mixture was evaporated to dryness under reduced pressure. The remaining solid was dissolved in dichloromethane, and the solution was poured into n-hexane(300 ml). The precipitated crystals were filtrated by suction, whereupon the title compound was obtained(0.87 g, 70.7% in yield) as yellow crystals.
m.p. 195°~215° C.

EXAMPLE 2

(Preparation of 7-ethyl-17-acetoxycamptothecin-21-(2-diethylamino)ethylamide)

(a) 7-Ethylcamptothecin(1.00 g, 2.66 mmol) was dissolved in N,N-diethylethylenediamine(20 ml), the reaction followed by the after-treatment was carried out with same manner as described in Example 1, whereby 7-ethyl-17-hydroxycamptothecin-21-(2-diethylamino)ethylamide was obtained.

(b) Acetyl chloride(173 μl, 2.44 mmol) was added to the ice-cooling solution of 7-ethyl-17-hydroxycamptothecin-21-(2-diethylamino)ethyl amide, obtained by step(a), in dichloromethane(20 ml), in the presence of 4-dimethylaminopyridine(100 mg, 0.82 mmol). After stirring for an hour under ice-cooling, water was added to the reaction mixture, and the aqueous phase was adjusted to weak basic conditions by adding 1N NaOH. After shaking, the organic phase was separated, washed with saturated aqueous solution of NaCl, dried over anhydrous $MgSO_4$, filtered, and then evaporated to dryness under reduced pressure. The residual material was purified through silica gel column chromatography with $CHCl_3$-MeOH as an eluent and crystallized from n-hexane to give the title compound as pale yellow crystals.
m.p. 177°~181° C.

EXAMPLE 3

(Preparation of 7-ethyl-17-benzoyloxycamptothecin-21-(2-diethylamino)ethylamide)

Using benzoyl chloride(311 μl, 2.44 mmol) as an acid chloride in place of acetyl chloride, the reaction followed by the after-treatment was carried out with same manner as described in example 2(b), whereby the title compound was obtained as yellow crystals.
m.p. 151°~164° C.
IR$\nu$(KBr)cm$^{-1}$;
3350,2930,1700,1650,1590,1510,1450,1270,1100,710.

EXAMPLE 4

(Preparation of 7-ethyl-17-propionyloxycamptothecin-21-(2-diethylamino)ethylamide)

Using propionyl chloride(212 μl, 2.44 mmol) as an acid chloride in place of acetyl chloride, the reaction followed by the after-treatment was carried out with same manner as described in example 2(b), whereby the title compound was obtained as pale yellow crystals.
m.p. 208°~209.5° C.
IR$\nu$(KBr)cm$^{-1}$;
3360,2960,1730,1650,1590,1520,1460,1180,760.

EXAMPLE 5

(Preparation of 7-ethyl-17-butyryloxycamptothecin-21-(2-diethylamino)ethylamide)

Using butyryl chloride(253 μl, 2.44 mmol) as an acid chloride in place of acetyl chloride, the reaction followed by the after-treatment was carried out with same manner as described in example 2(b), whereby the title compound was obtained as pale yellow crystals.
m.p. 150°~154° C.
IR$\nu$(KBr)cm$^{-1}$;
3370,2960,1730,1650,1590,1520,1180,760.

EXAMPLE 6

(Preparation of 7-ethyl-17-butyryloxycamptothecin-21-(2-dimethylamino)ethylamide)

Using 21-(2-dimethylamino)ethylamide derivative and butyryl chloride(269 μl, 2.59 mmol) in place of 21-(2-diethylamino)ethylamide derivative and acetyl chloride, the reaction followed by the after-treatment was carried out with same manner as described in example 2(b), whereby the title compound was obtained as pale yellow crystals.

m.p. 164.5°~166.5° C.
IRν(KBr)cm⁻¹;
3370,2960,1730,1650,1590,1520,1460,1180,760.

EXAMPLE 7

(Preparation of
7-ethyl-17-benzoyloxycamptothecin-21-(2-dimethylamino)ethylamide)

Using benzoyl chloride(331 μl, 2.59 mmol) as an acid chloride, the reaction followed by the after-treatment was carried out with same manner as described in example 6, whereby the title compound was obtained as pale yellow crystals(142 mg, 11.6% in yield).
m.p. 172°~176° C.
IRν(KBr)cm⁻¹;
3350,2980,1710,1640,1590,1500,1450,1270,1100,715.
NMR(in CDCl$_3$)δppm; 1.09(3H,t,J=7.3Hz,20-CH$_2$CH$_3$), 1.35(3H,t,J=7.7 Hz, 7-CH$_2$CH$_3$),2.18(6H,s,—N(CH$_3$)$_2$),2.34~2.41(3H,-m,—CH$_2$CH$_2$N= and 20-CHH'CH$_3$), 2.44~2.51(1H,m,20-CHH'CH$_3$),3.08~3.14(2H,m,7-CH$_2$CH$_3$),3.19~3.25(1H,m,—NHCHH'CH$_2$N=),3.32~3.39(1H,m,—NHCHH'CH$_2$N=),5.15(2H,dd,J=18.7 Hz, 5-H$_2$), 5.76 and 5.87(two 1H's,d,J=11.7 Hz, 17-H$_2$),7.35~7.39(3H,m,17-O-(C=O)Ph and —NHCH$_2$CH$_2$N=),7.50(1H,t,J=7.3 Hz, 17-O(C=O)Ph),7.55(1H,t,J= 7.3 Hz,10-H),7.63(1H,s,14-H),7.73(1H,t,J=7.0 Hz,11-H),7.93(1H,d,J=8.4 Hz, 9-H),8.03(2H,d,J=7.3 Hz,17-O(C=O)Ph),8.13(1H,d,J=8.4 Hz,12-H).

EXAMPLE 8

(Preparation of
7-ethyl-17-(4-methoxybenzoyloxy)camptothecin-21-(2-dimethylamino)ethylamide)

Using 4-methoxybenzoyl chloride(363 μl, 2.59 mmol) as an acid chloride, the reaction followed by the after-treatment was carried out with same manner as described in example 6, whereby the title compound was obtained as pale yellow crystals(224 mg, 17.4% in yield).
m.p. 176°~177.5° C.
IRν(KBr)cm⁻¹;
3400,3300,2960,1690,1660,1640,1600,1500,1450,1260,1240,1160,1090,760.
NMR(in CDCl$_3$)δppm; 1.08(3H,t,J=7.3 Hz, 20-CH$_2$CH$_3$),1.36(3H,t,J=7.7 Hz,7-CH$_2$CH$_3$),2.24(6H,s,—N(CH$_3$)$_2$),2.36~2.49(4H,-m,—CH$_2$CH$_2$N= and 20-CH$_2$CH$_3$), 3.12(2H,q,7-CH$_2$CH$_3$),3.21~3.27and 3.37~3.42(two 1H's,m,—NHCH$_2$CH$_2$N=),
3.82(3H,s,—OCH$_3$),5.17(2H,dd,5-H$_2$),5.70 and 5.85(two 1H's,d,J=11.7 Hz, 17-H$_2$),6.85(2H,d,J=8.8 Hz,Arom),7.57(1H,t,10-H),7.64(1H,s,14-H),7.74 (1H,t,11-H),7.96~8.00(3H,m,9-H and Arom),8.15(1H,d,12-H).

EXAMPLE 9

(Preparation of
7-ethyl-17-(4-fluorobenzoyloxy)camptothecin-21-(2-dimethylamino)ethylamide)

Using 4-fluorobenzoyl chloride(305 μl, 2.59 mmol) as an acid chloride, the reaction followed by the after-treatment was carried out with same manner as described in example 6, whereby the title compound was obtained as pale yellow crystals(613 mg, 48.5% in yield).

m.p. 167.2°~169.5° C.
IRν(KBr)cm⁻¹;
3400,2970,1710,1650,1600,1500,1455,1270,1110,765.
NMR(in CDCl$_3$)δppm; 1.14(3H,t,J=7.3 Hz,20-CH$_2$CH$_3$),1.27(3H,t,J=7.3 Hz,7-CH$_2$CH$_3$),2.17(6H,s,—N(CH$_3$)$_2$),2.32~2.44(3H,-m,—CH$_2$CH$_2$N= and 20-CHH'CH$_3$), 2.57~2.64(1H,m,20-CHH'CH$_3$),2.89~3.01(2H,m,7-CH$_2$CH$_3$),3.07~3.15 and 3.33~3.41(two 1H's,m,—NHCH$_2$CH$_2$N=),4.97(2H,dd,J=18.3 Hz,5-H$_2$),5.80(2H,d,J=11.7 Hz,17-H$_2$),7.00(2H,t,J=8.8 Hz,Arom),7.35(1H,t,J=7.3 Hz,10-H),7.59 (1H,s,14-H),7.61(1H,d,9-H),7.70(1H,t,11-H),7.94(1H,d,J=8.1 Hz,12-H), 8.02(2H,dd,Arom).

EXAMPLE 10

(Preparation of
7-ethyl-17-(4-bromobenzoyloxy)camptothecin-21-(2-dimethylamino)ethylamide)

Using 4-bromobenzoyl chloride(568 mg, 2.59 mmol) as an acid chloride, the reaction followed by the after-treatment was carried out with same manner as described in example 6, whereby the title compound was obtained as pale yellow crystals(926 mg, 66.4% in yield).
m.p. 176°~179.5° C.
IRν(KBr)cm⁻¹;
3350,2980,1710,1670,1650,1595,1510,1450,1270,1095,760. NMR(in CDCl$_3$)δppm; 0.95(3H,t,J=7.3 Hz,20-CH$_2$CH$_3$),1.30(3H,t,J=7.3 Hz,7-CH$_2$CH$_3$),2.39~2.48(2H,m,20-CH$_2$CH$_3$),2.77(6H,s,—N(CH$_3$)$_2$),2.99~3.22(4H,-m,—CH$_2$CH$_2$N= and 7-CH$_2$CH$_3$),3.36~3.44 and 3.88~3.93(two 1H's,m,—NHCH$_2$CH$_2$N=),5.09(2H,dd,J=19.1 Hz,5-H$_2$),5.76(2H,dd,J=11.7 Hz,17-H$_2$),7.41(2H,d,Arom),7.54(1H,t,10-H),7.75~7.79(2H,m,14-H and 11-H),7.92(1H,d,9-H),8.05(1H,d,12-H),8.20(1H,br,—NHCH$_2$CH$_2$N=).

EXAMPLE 11

(Preparation of
7-ethyl-17-(2-bromobenzoyloxy)camptothecin-21-(2-dimethylamino)ethylamide)

Using 2-bromobenzoyl chloride(568 mg, 2.59 mmol) as an acid chloride, the reaction followed by the after-treatment was carried out with same manner as described in example 6, whereby the title compound was obtained as pale yellow crystals(324 mg, 24.5% in yield).
m.p. 180°~183.5° C.
IRν(KBr)cm⁻¹;
3380,3250,2980,1710,1670,1595,1510,1460,1240,1140,1100,940.
NMR(in CDCl$_3$)δppm; 1.14(3H,t,J=7.3 Hz,20-CH$_2$CH$_3$),1.31(3H,t,J=7.3 Hz,7-CH$_2$CH$_3$),2.16(6H,s,—N(CH$_3$)$_2$),2.29~2.41(3H,-m,—CH$_2$CH$_2$N= and 20-CHH'CH$_3$), 2.54~2.63(1H,m,20-CHH'CH$_3$),2.94~3.19(3H,m,7-CH$_2$CH$_3$ and —NHCHH'CH$_2$-N=),3.32~3.38(1H,m,—NHCHH'CH$_2$N=),5.05(2H,-dd,J=19.1 Hz,5-H$_2$),5.80(2H,s,17-H$_2$),7.41(1H,t,10-H),7.46~7.49(2H,m,Arom),7.54(1H,-t,—NH—),7.58(1H,s,14-H),7.65(1H,t,11-H),7.71(1H,d,9-H),7.84~7.87(2H,m,Arom),8.00(1H,d,J=7.3 Hz,12-H).

EXAMPLE 12

(Preparation of 7-ethyl-17-propionyloxycamptothecin-21-(2-dimethylamino)ethylamide)

Using propionyl chloride(225 μl, 2.59 mmol) as an acid chloride, the reaction followed by the after-treatment was carried out with same manner as described in example 6, whereby the title compound was obtained as pale yellow crystals(535 mg, 47.7% in yield).

m.p. 137°~154° C.

IRν(KBr)cm$^{-1}$; 3360,2970,1760,1730,1650,1595,1510,1460,1170,1130,1070.

NMR(in CDCl$_3$)δppm; 1.12(6H,t,J=7.3 Hz,20-CH$_2$CH$_3$ and 17-O(C=O)CH$_2$CH$_3$), 1.30(3H,t,J=7.3 Hz,7-CH$_2$CH$_3$),2.26(6H,s,—N(CH$_3$)$_2$),2.28~2.37(3H,-m,—CH$_2$-CH$_2$N= and 20-CHH'CH$_3$),2.42~2.56(3H,m,20-CHH'CH$_3$ and 17-O(C=O)CH$_2$CH$_3$), 2.91~3.06(2H,m,7-CH$_2$CH$_3$),3.25~3.33 and 3.43~3.51(two 1H's,m,—NHCH$_2$-CH$_2$N=),4.99(2H,dd,J=18.3 Hz,5-H$_2$),5.49(2H,d,J=11.7 Hz,17-H$_2$),7.41(1H,t,10-H),7.53(1H,s,14-H),7.65(1H,t,11-H),7.71(1H,d,9-H),7.99(1H,d,12-H).

EXAMPLE 13

(Preparation of 7-ethyl-17-(4-chlorobenzoyloxy)camptothecin-21-(2-dimethylamino)ethylamide)

Using 4-chlorobenzoyl chloride(329 μl, 2.59 mmol) as an acid chloride, the reaction followed by the after-treatment was carried out with same manner as described in example 6, whereby the title compound was obtained as pale yellow crystals(613 mg, 47.2% in yield).

m.p. 167°~188° C.

IRν(KBr)cm$^{-1}$; 3360,2970,1710,1670,1650,1590,1510,1450,1280,1090.

EXAMPLE 14

(Preparation of 7-ethyl-17-(4-nitrobenzoyloxy)camptothecin-21-(2-dimethylamino)ethylamide and its methanesulfonate)

To the ice-cooling solution of 7-Ethyl-17-hydroxycamptothecin-21-(2-dimethylamino)ethylamide(1.00 g, 2.15 mmol) in dichloromethane(20 ml), 4-N,N-dimethylaminopyridine(100 mg, 0.82 mmol) and 4-nitrobenzoyl chloride(1.20 g, 6.45 mmol) were added. After stirring under ice-cooling for an hour, the reaction mixture was dilluted with dichloromethane, washed with a saturated aqueous solution of NaHCO$_3$ and with a saturated aqueous solution of NaCl. The organic phase was separated, dried over anhydrous MgSO$_4$, filtered, and then evaporated to dryness under reduced pressure. The residual material was purified through silica gel column chromatography with CHCl$_3$-MeOH as an eluent and crystallized from CHCl$_3$-n-hexane to give the title compound(633 mg, 47.9% in yield) as pale yellow powder.

m.p. 153°~158° C.(dec.)

IRν(KBr)cm$^{-1}$; 3380,2960,2940,1717,1650,1580,1525,1270.

NMR(CDCl$_3$)δppm; 1.13(3H,t,J=7.3 Hz, 20-CH$_2$CH$_3$),1.35(3H,t,J=7.7 Hz,7-CH$_2$-CH$_3$),2.16(6H,s,—N(CH$_3$)$_2$),2.27~2.61(4H,-m,—CH$_2$CH$_2$N= and 20-CH$_2$CH$_3$), 3.00~3.39(4H,m,7-CH$_2$CH$_3$ and NHCH$_2$CH$_2$N=),5.13(2H,dd,J=19.1 Hz,5-H$_2$), 5.36(1H,br,20-OH),5.85(2H,dd,J=11.7 Hz,17-H$_2$),7.37(1H,br-t,J=5.1 Hz,NHCH$_2$CH$_2$N=),7.51(1H,t,10-H),7.59(1H,s,14-H),7.71(1H,t,11-H),7.86(1H,d,9-H),8.09(1H,d,12-H),8.15~8.25(4H,m,—C$_6$H$_4$-p-NO$_2$).

Methanesulfonate

To the CHCl$_3$ solution of free compound(200 mg, 0.33 mmol) the 0.1M THF solution of methanesulfonic acid(5.0 ml) was added. Then n-hexane (20 ml) was added to the solution and the resulting precipitated crystals were filtrated and dried to give yellow crystals of methanesulfonate in quantitative yield.

IRν(KBr)cm$^{-1}$; 3380,2685,1715,1650,1605,1520,1270,1200.

NMR(DMSO-d$_6$)δppm; 0.92(3H,t,J=7.3 Hz,20-CH$_2$CH$_3$),1.33(3H,t,J=7.7 Hz,7-CH$_2$-CH$_3$),2.18~2.29(2H,m,20-CH$_2$CH$_3$),2.31(3H,s,CH$_3$SO$_3$—),2.74 and 2.75(two 3H's,s,NH+(CH$_3$)$_2$),3.01~3.50(6H,m,7-CH$_2$CH$_3$ and NHCH$_2$CH$_2$NH+=),5.36(2H,s,5-H$_2$),5.70(2H,dd,J=11.0 Hz,17-H$_2$),6.35~6.49(1H,br,20-OH),7.53(1H,s,14-H),7.75(1H,t,10-H),7.87(1H,t,11-H),8.14 and 8.36(two 2H's,d,J=8.8 Hz,—C$_6$H$_4$-p-NO$_2$),8.20(1H,d,9-H),8.33(1H,d,12-H),8.47(1H,t,J=5.9 Hz,-NHCH$_2$-CH$_2$NH+=),9.14~9.34(1,br,—NH+=).

EXAMPLE 15

(Preparation of 7-ethyl-17-(4-trifluoromethylbenzoyloxy)camptothecin-21-(2-dimethylamino)ethylamide, its methanesulfonate, and hydrochloride)

Using 4-trifluoromethylbenzoyl chloride(1.35 g, 6.45 mmol) as an acid chloride in place of 4-nitrobenzoylchloride, the reaction followed by the after-treatment was carried out with same manner as described in example 14, whereby the pale yellow solid of title compound(916 mg, 66.9% in yield) was obtained.

m.p. 144°~148° C. (dec.).

IRν(KBr)cm$^{-1}$; 3360,2960,2930,1715,1650,1595,1510,1325,1275,1165,1125,1100.

Methanesulfonate

To the CHCl$_3$ solution of free compound(200 mg) the 0.1M THF solution of methanesulfonic acid(4.7 ml) was added. Then n-hexane(20 ml) was added to the solution and the resulting precipitated crystals were collected by filtration and dried to give yellow crystals of methanesulfonate in quantitative yield.

IRν(KBr)cm$^{-1}$; 3380,2670,1715,1650,1610,1325,1275,1195,1120,1055.

NMR(DMSO-d$_6$)δppm; 0.91(3H,t,J=7.3 Hz,20-CH$_2$CH$_3$),1.33(3H,t,J=7.7 Hz,7-CH$_2$-CH$_3$),2.24(2H,q,20-CH$_2$CH$_3$),2.34(3H,s,CH$_3$SO$_3$—),2.74 and 2.75(two 3H's,s,NH+(CH$_3$)$_2$),3.04~3.49(6H,m,7-CH$_2$CH$_3$ and —NHCH$_2$CH$_2$NH+=),5.35(2H,s,5-H$_2$),5.69(2H,dd,J=11.0 Hz,17-H$_2$),6.22~6.60(1H,br,20-OH),7.54(1H,s,14-H),7.75(1H,t,10-H),7.87(1H,t,11-H),7.91 and 8.11(two 2H's,d,—C$_6$H$_4$-p-CF$_3$),8.20(1H,d,9-H),8.31(1H,d,12-H),8.47(1H,t,J=5.9 Hz,NHCH$_2$CH$_2$NH+=),9.17~9.37(1H,br,—NH+=).

Hydrochloride

To the suspension of free compound(200 mg) in distilled water(5 ml) the 0.1N HCl(3.8 ml) was added. An insoluble materials were filtered off and the filtrate was lyophilized to give the hydrochloride as a yellow amorphous in quantitative yield.

IR$\nu$(KBr)cm$^{-1}$;
3360,2670,1715,1650,1595,1510,1325,1275,1120,1100.

NMR(DMSO-d$_6$)$\delta$ppm; 0.89(3H,t,J=7.3 Hz,20-CH$_2$CH$_3$),1.32(3H,t,J=7.7 Hz,7-CH$_2$CH$_3$),2.26(2H,q,20-CH$_2$CH$_3$),2.72 and 2.73(two 3H's,s,NH$^+$=(CH$_3$)$_2$),3.00~3.56(6H,m,7-CH$_2$CH$_3$ and NHCH$_2$CH$_2$NH$^+$=),5.34(2H,s,5-H$_2$),5.71(2H,dd,J=11.0 Hz,17-H$_2$),6.35~6.70(1H,br,20-OH),7.57(1H,s,14-H),7.75(1H,t,10-H),7.87(1H,t,11-H),7.91 and 8.10(two 2H's,d,—C$_6$H$_4$-p-CF$_3$),8.20(1H,d,9-H),8.30(1H,d,12-H),8.48(1H,t,J=5.9 Hz,—NHCH$_2$CH$_2$NH$^+$=),9.90~10.10(1H,br,—NH$^+$=).

EXAMPLE 16

(Preparation of
7-ethyl-17-(4-iodobenzoyloxy)camptothecin-21-(2-dimethylamino)ethylamide and its methanesulfonate)

Using 4-iodobenzoyl chloride(1.00 g, 3.75 mmol) as an acid chloride in place of 4-nitrobenzoyl chloride, the reaction followed by the after-treatment was carried out with same manner as described in example 14, whereby the pale yellow solid of title compound(648 mg, 43.2% in yield) was obtained.

m.p. 146°~150° C. (dec.)
IR$\nu$(KBr)cm$^{-1}$;
3370,2960,2930,1710,1650,1585,1510,1270,1100.

Methanesulfonate

To the CHCl$_3$ solution of free compound(200 mg) the 0.1M THF solution of methanesulfonic acid(4.2 ml) was added. Then n-hexane(20 ml) was added to the solution and the resulting precipitated crystals were filtered and dried to give yellow crystals of methanesulfonate in quantitative yield.

IR$\nu$(KBr)cm$^{-1}$;
3360,2670,1710,1650,1610,1585,1270,1195,1055.

NMR(DMSO-d$_6$)$\delta$ppm; 0.90(3H,t,J=7.3 Hz,20-CH$_2$CH$_3$),1.33(3H,t,J=7.7 Hz,7-CH$_2$CH$_3$),2.23(2H,m,20-CH$_2$CH$_3$),2.33(3H,s,CH$_3$SO$_3$—),2.74 and 2.75(two 3H's,s,NH$^+$(CH$_3$)$_2$),3.02~3.48(6H,m,7-CH$_2$CH$_3$ and NHCH$_2$CH$_2$NH$^+$=),5.35(2H,s,5-H$_2$),5.61(2H,dd,J=11.0 Hz,17-H$_2$),6.24~6.55(1H,br,20-OH),7.52(1H,s,14-H),7.66 and 7.91(two 2H's,d,C$_6$H$_4$-p-I),7.75(1H,t,10-H),7.87(1H,t,11-H),8.19(1H,d,9-H),8.30(1H,d,12-H),8.45(1H,t,J=5.5 Hz,NHCH$_2$CH$_2$NH$^+$=),9.19~9.35(1H,br,—NH$^+$=).

EXAMPLE 17

(Preparation of
7-ethyl-17-(1-naphtoyloxy)camptothecin-21-(2-dimethylamino)ethylamide and its hydrochloride)

Using 1-naphtoyl chloride(615 mg, 3.23 mmol) as an acid chloride, the reaction followed by the after-treatment was carried out with same manner as described in example 14, whereby the yellow crystals of title compound(371 mg, 27.9% in yield)were obtained.

m.p. 144°~147° C. (dec.)
IR$\nu$(KBr)cm$^{-1}$;
3380,2960,2925,1705,1650,1595,1510,1275,1240,1195,1135.

Hydrochloride

To the suspension of free compound(200 mg) in distilled water(15 ml) the 0.1N HCl(3.9 ml) was added. An insoluble materials were filtered off and the filtrate was lyophilized to give the hydrochloride as a yellow amorphous(193 mg, 91.0% in yield).

IR$\nu$(KBr)cm$^{-1}$;
3380,1700,1650,1590,1510,1275,1240,1195,1135.

NMR(DMSO-d$_6$)$\delta$ppm; 0.90(3H,t,J=7.3 Hz,20-CH$_2$CH$_3$),1.33(3H,t,J=7.7 Hz,7-CH$_2$CH$_3$),2.29(2H,q,20-CH$_2$CH$_3$),2.70 and 2.71(two 3H's,s,NH$^+$=(CH$_3$)$_2$),3.04~3.57(6H,m,7-CH$_2$CH$_3$ and NHCH$_2$CH$_2$NH$^+$=),5.35(2H,s,5-H$_2$),5.74(2H,dd,J=11.0 Hz,17-H$_2$),6.40~6.60(1H,br,20-OH),7.51~7.71(4H,m,14-H and Napht),7.73(1H,t,10-H),7.86(1H,t,11-H),7.97~8.09(2H,m,Napht),8.12~8.23(2H,m,9-H and Napht),8.29(1H,d,12-H),8.48(1H,t,J=5.5 Hz,NHCH$_2$CH$_2$NH$^+$=),8.83(1H,d,J=8.4 Hz,Napht),9.98~10.12(1H,br,NH$^+$=).

EXAMPLE 18

(Preparation of
7-ethyl-17-(2-naphtoyloxy)camptothecin-21-(2-dimethylamino)ethylamide and its hydrochloride)

Using 2-naphtoyl chloride(615 mg, 3.23 mmol) as an acid chloride, the reaction followed by the after-treatment was carried out with same manner as described in example 14, whereby the pale yellow crystals of title compound(538 mg, 40.4% in yield) were obtained.

m.p. 179°~183° C. (dec.)
IR$\nu$(KBr)cm$^{-1}$;
3370,2970,2930,1700,1650,1590,1510,1455,1275,1220,1195.

Hydrochloride

To the suspension of free compound(200 mg) in distilled water(15 ml) the 0.1N HCl(3.9 ml) was added. An insoluble materials were filtered off and the filtrate was lyophilized to give the hydrochloride as a yellow amorphous in quantitative yield.

IR$\nu$(KBr)cm$^{-1}$;
3380,1705,1650,1595,1280,1225,1195.

NMR(DMSO-d$_6$)$\delta$ppm; 0.92(3H,t,J=7.3 Hz,20-CH$_2$CH$_3$),1.32(3H,t,J=7.7 Hz,7-CH$_2$CH$_3$),2.18~2.40(2H,q,20-CH$_2$CH$_3$),2.70 and 2.71(two 3H's,s,NH$^+$(CH$_3$)$_2$),3.02~3.57 (6H,m,7-CH$_2$CH$_3$ and NHCH$_2$CH$_2$NH$^+$=),5.34(2H,s,5-H$_2$),5.74(2H,dd,J=11.0 Hz,17-H$_2$),6.25~6.80(1H,br,20-OH),7.55~7.70(3H,m,14-H and Napht),7.74(1H,t,10-H),7.87(1H,t,11-H),7.92~8.13(4H,m,Napht),8.21(1H,d,9-H),8.29(1H,d,12-H),8.50(1H,t,J=5.5 Hz, —NHCH$_2$CH$_2$NH$^+$=),8.56(1H,s,-Napht),10.16~10.34(1H,br,NH$^+$=).

EXAMPLE 19

(Preparation of
7-ethyl-17-(2-furoyloxy)camptothecin-21-(2-dimethylamino)ethylamide and its hydrochloride)

Using 2-furoyl chloride(422 mg, 3.23 mmol) as an acid chloride, the reaction followed by the after-treatment was carried out with same manner as described in example 14, whereby the yellow crystals of title compound(662 mg, 55.1% in yield) were obtained.

m.p. ~151° C. (dec.)

IRν(KBr)cm⁻¹;
3380,1710,1650,1595,1295,1175,1115.

Hydrochloride

To the suspension of free compound(200 mg) in distilled water(15 ml) the 0.1N HCl(4.3 ml) was added. An insoluble materials were filtered off and the filtrate was lyophilized to give the hydrochloride as a yellow amorphous in quantitative yield.
IRν(KBr)cm⁻¹;
3300,2950,1710,1650,1600,1510,1470,1295,1175,1110.
NMR(DMSO-$d_6$)δppm; 0.87(3H,t,J=7.3 Hz,20-C$\underline{H_2}$CH$_3$),1.32(3H,t,J=7.7 Hz,7-CH$_2$C$\underline{H_3}$),2.10~2.35(2H,m,20-C$\underline{H_2}$CH$_3$),2.72 and 2.73(two 3H's,s,NH⁺(C$\underline{H_3}$)$_2$),3.04~3.64(6H,m,7-C$\underline{H_2}$CH$_3$ and NHC$\underline{H_2}$C$\underline{H_2}$NH⁺=),5.31(2H,s,5-H$_2$),5.64(2H,dd,J=11.0 Hz,17-H$_2$),6.28~6.66(1H,br,20-OH),6.66(1H,dd,J=1.8 and 3.3 Hz,Furano),7.20(1H,d,Furano),7.57(1H,s,14-H),7.73(1H,t,10-H),7.86(1H,t,11-H),7.94(1H,d,Furano),8.19(1H,d,9-H),8.28(1H,d,12-H),8.45(1H,t,J=5.5 Hz,—N$\underline{H}$CH$_2$CH$_2$NH⁺=),10.22~10.42(1H,br,NH⁺=).

EXAMPLE 20

(Preparation of 7-ethyl-17-(2-thenoyloxy)camptothecin-21-(2-dimethylamino)ethylamide and its hydrochloride)

Using 2-thenoyl chloride(474 mg, 3.23 mmol) as an acid chloride, the reaction followed by the after-treatment was carried out with same manner as described in example 14, whereby the yellow crystals of title compound(480 mg, 38.8% in yield) were obtained.
m.p. 149°~155° C. (dec.)
IRν(KBr)cm⁻¹;
3370,2970,2960,1695,1645,1595,1515,1260,1090.

Hydrochloride

To the suspension of free compound(200 mg) in distilled water(15 ml) the 0.1N HCl(4.2 ml) was added. An insoluble materials were filtered off and the filtrate was lyophilized to give the hydrochloride as a yellow amorphous in quantitative yield.
IRν(KBr)cm⁻¹;
3370,2670,1695,1645,1590,1520,1260,1090.
NMR(DMSO-$d_6$)δppm; 0.88(3H,t,J=7.3 Hz,20-C$\underline{H_2}$CH$_3$),1.32(3H,t,J=7.7 Hz,7-CH$_2$C$\underline{H_3}$),2.13~2.38(2H,m,20-C$\underline{H_2}$CH$_3$),2.72 and 2.74(two 3H's,s,NH⁺(C$\underline{H_3}$)$_2$),3.04~3.67(6H,m,7-C$\underline{H_2}$CH$_3$ and NHC$\underline{H_2}$C$\underline{H_2}$NH⁺=),5.32(2H,s,5-H$_2$),5.66(2H,s,17-H$_2$),6.20~6.74(1H,br,20-OH),7.68~7.79(1H,m,Thiopheno),7.59(1H,s,14-H),7.67~7.80(2H,m,10-H and Thiopheno),7.86(1H,t,11-H),7.91(1H,d,J=5.1 Hz,Thiopheno),8.19(1H,d,9-H),8.29(1H,d,12-H),8.46(1H,t,J=5.5 Hz,N$\underline{H}$CH$_2$CH$_2$NH⁺=),10.16~10.35(1H,br,NH⁺=).

EXAMPLE 21

(Preparation of 7-ethyl-17-cyclopropanecarbonyloxycamptothecin-21-(2-dimethylamino)ethylamide and its hydrochloride)

Using cyclopropanecarbonyl chloride(338 mg, 3.23 mmol) as an acid chloride, the reaction followed by the after-treatment was carried out with same manner as described in example 14, whereby the yellow crystals of title compound(216 mg, 18.8% in yield) were obtained.
m.p. 147°~150° C. (dec.)
IRν(KBr)cm⁻¹;
3375,2965,2930,1715,1645,1595,1515,1455,1395,1175.

Hydrochloride

To the suspension of free compound(150 mg) in distilled water(15 ml) the 0.1N HCl(3.4 ml) was added. An insoluble materials were filtered off and the filtrate was lyophilized to give the hydrochloride as a yellow amorphous in quantitative yield.
IRν(KBr)cm⁻¹;
3370,2670,1710,1645,1595,1515,1395,1175.
NMR(DMSO-$d_6$)δppm;0.74~0.97(7H,m,20-C$\underline{H_2}$CH$_3$ and cyclo-Pr),1.33(3H,t,J=7.3 Hz,7-CH$_2$C$\underline{H_3}$),1.52~1.62(1H,m,cyclo-Pr),2.10~2.31(2H,m,20-C$\underline{H_2}$CH$_3$), 2.76 and 2.77(two 3H's,s,NH⁺(C$\underline{H_3}$)$_2$),3.05~3.35(6H,m,7-C$\underline{H_2}$CH$_3$ and NHC$\underline{H_2}$C$\underline{H_2}$NH⁺=),5.32(2H,s,5-H$_2$),5.37(2H,d,J=11.0 Hz,17-H$_2$),6.28~6.58 (1H,br,20-OH),7.54(1H,s,14-H),7.74(1H,t,10-H),7.86(1H,t,11-H),8.19(1H,d,9-H),8.30(1H,d,12-H),8.40(1H,t,J=5.1 Hz,—N$\underline{H}$CH$_2$CH$_2$NH⁺=),10.08~10.28(1H,br,NH⁺=).

EXAMPLE 22

(Preparation of 7-ethyl-17-(3-fluorobenzoyloxy)camptothecin-21-(2-dimethylamino)ethylamide and its hydrochloride)

Using 3-fluorobenzoyl chloride(512 mg, 3.23 mmol) as an acid chloride, the reaction followed by the after-treatment was carried out with same manner as described in example 14, whereby the pale yellow crystals of title compound(348 mg, 27.6% in yield) were obtained.
m.p. 132°~138° C. (dec.)
IRν(KBr)cm⁻¹;
3370,2970,2930,1715,1650,1590,1510,1445,1275,1200.

Hydrochloride

To the suspension of free compound(200 mg) in distilled water(15 ml) the 0.1N HCl(4.1 ml) was added. An insoluble materials were filtered off and the filtrate was lyophilized to give the hydrochloride as a yellow amorphous in quantitative yield.
IRν(KBr)cm⁻¹;
3380,2670,1710,1650,1590,1510,1445,1275,1200.
NMR(DMSO-$d_6$)δppm;0.89(3H,t,J=7.3 Hz,20-C$\underline{H_2}$CH$_3$),1.32(3H,t,J=7.3 Hz,7-CH$_2$C$\underline{H_3}$),2.26(2H,q,20-C$\underline{H_2}$CH$_3$),2.72 and 2.74(two 3H's,s,NH⁺(C$\underline{H_3}$)$_2$),3.05~3.31(6H,m,7-C$\underline{H_2}$CH$_3$ and NHC$\underline{H_2}$C$\underline{H_2}$NH⁺=),5.34(2H,s,5-H$_2$),5.68(2H,dd,J=11.0 Hz,17-H$_2$),6.38~6.60(1H,br,20-OH),7.46~7.67(4H,m,14-H and Arom), 7.70~7.80(2H,10-H and Arom),7.87(1H,t,11-H),8.20(1H,d,9-H),8.30(1H,d,12-H),8.48(1H,t,J=5.5 Hz,—N$\underline{H}$CH$_2$NH⁺=),10.01~10.21(1-H,—N$\underline{H}$CH$_2$CH$_2$NH⁺=).

EXAMPLE 23

(Preparation of 7-ethyl-17-(2-fluorobenzoyloxy)camptothecin-21-(2-dimethylamino)ethylamide and its hydrochloride)

Using 2-fluorobenzoyl chloride(512 mg, 3.23 mmol) as an acid chloride, the reaction followed by the after-treatment was carried out with same manner as described in example 14, whereby the pale yellow crystals of title compound(445 mg, 35.2% in yield) were obtained.

m.p. 154°~160° C. (dec.)
IRν(KBr)cm$^{-1}$;
3360,2960,2930,1715,1650,1610,1510,1450,1295,1250.

Hydrochloride

To the suspension of free compound(200 mg) in distilled water(15 ml) the 0.1N HCl(4.1 ml) was added. An insoluble materials were filtered off and the filtrate was lyophilized to give the hydrochloride as a yellow amorphous in quantitative yield.

IRν(KBr)cm$^{-1}$;
3360,2670,1710,1650,1610,1515,1450,1295,1250,1220,11-20,1080.

NMR(DMSO-d$_6$)δppm;0.87(3H,t,J=7.0 Hz,20-CH$_2$CH$_3$),1.32(3H,t,J=7.7 Hz,7-CH$_2$CH$_3$),2.18~2.33(2H,m,20-CH$_2$CH$_3$),2.73 and 2.74(two 3H's,s,NH$^+$(CH$_3$)$_2$),3.05~3.60(6H,m,7-CH$_2$CH$_3$ and NHCH$_2$CH$_2$NH$^+$=),5.32(2H,s,5-H$_2$),5.67(2H,dd,J=11.0 Hz,17-H$_2$),6.36~6.60(1H,br,20-OH),7.23~7.38(2H,m,Arom),7.57(1H,s,14-H),7.60~7.69(1H,m,Arom),7.74(1H,t,10-H),7.78~7.92(2H,m,11-H and Arom),8.19(1H,d,9-H),8.29(1H,d,12-H),8.46(1H,t,J=5.5 Hz,—NHCH$_2$CH$_2$NH$^+$=),10.04~10.26(1H,—NHCH$_2$CH$_2$NH$^+$=).

EXAMPLE 24

(Preparation of 7-ethyl-17-(trans-4-benzyloxycarbonylaminomethylcyclohexanecarbonyloxy)camptothecin-21-(2-dimethylamino)ethylamide and its hydrochloride)

Using trans-4-benzyloxycarbonylaminomethylcyclohexanecarbonyl chloride(2.00 g, 6.46 mmol) as an acid chloride, the reaction followed by the after-treatment was carried out with same manner as described in example 14, whereby the pale yellow crystals of title compound(1.00 g, 31.6% in yield) were obtained.

m.p. ~112° C. (dec.)
IRν(KBr)cm$^{-1}$;
3310,2925,1715,1650,1595,1510,1450,1250,1170,1140.

Hydrochloride

To the suspension of free compound(200 mg) in distilled water(15 ml) the 0.1N HCl(2.9 ml) was added. An insoluble materials were filtered off and the filtrate was lyophilized to give the hydrochloride as a yellow amorphous in quantitative yield.

IRν(KBr)cm$^{-1}$;
3280,2920,2590,1710,1650,1600,1510,1450,1235,1170,11-40.

NMR(DMSO-d$_6$)δppm;0.74~0.98(5H,m,20-CH$_2$CH$_3$ and cyclo-Hex),1.18~1.43(6H,m,7-CH$_2$CH$_3$ and cyclo-Hex),1.61~1.78(2H,m,cyclo-Hex),1.81~1.98(2H,m,cyclo-Hex),2.08~2.28(3H,m,20-CH$_2$CH$_3$ and cyclo-Hex),2.75 and 2.76(two 3H's,s,NH$^+$(CH$_3$)$_2$),2.83(2H,t-like,cyclo-Hex-CH$_2$NHCO$_2$CH$_2$Ph),3.05~3.63(6H,m,7-CH$_2$CH$_3$ and NHCH$_2$CH$_2$NH$^+$=),4.98(2H,s,CO$_2$CH$_2$Ph),5.30(2H,s,5-H$_2$),5.34(2H,dd,J=11.0 Hz,17-H$_2$),6.37(1H,s,20-OH), 7.23(1H,t,cyclo-Hex-CH$_2$NHCO$_2$C H$_2$Ph),7.25~7.40(5H,m,Ph),7.55(1H,s,14-H),7.73(1H,t,10-H),7.85(1H,t,11-H),8.17(1H,d,9-H),8.28(1H,d,12-H),8.37(1H,t,J=5.5 Hz,—NHCH$_2$CH$_2$NH$^+$=),9.98~10.14(1H,br,—NHCH$_2$CH$_2$NH$^+$=).

EXAMPLE 25

(Preparation of 7-ethyl-17-crotonyloxycamptothecin-21-(2-dimethylamino)ethylamide and its hydrochloride)

Using crotonyl chloride(337 mg, 3.23 mmol) as an acid chloride, the reaction followed by the after-treatment was carried out with same manner as described in example 14, whereby the pale yellow crystals of title compound(230 mg, 20.1% in yield) were obtained.

m.p. 147°~148° C. (dec.)
IRν(KBr)cm$^{-1}$;
3355,2970,2960,1710,1650,1595,1510,1180.

Hydrochloride

To the suspension of free compound(160 mg) in distilled water(10 ml) the 0.1N HCl(3.6 ml) was added. An insoluble materials were filtered off and the filtrate was lyophilized to give the hydrochloride as a yellow amorphous in quantitative yield.

IRν(KBr)cm$^{-1}$;
3380,2670,1705,1650,1595,1515,1180.

NMR(DMSO-d$_6$)δppm;0.86(3H,t,J=7.3 Hz,20-CH$_2$CH$_3$),1.33(3H,t,J=7.7 Hz,7-CH$_2$CH$_3$),1.85(3H,d,J=7.0 Hz,CH=CHCH$_3$),2.21(2H,q,20-CH$_2$CH$_3$),2.75 and 2.76(two 3H's,s,NH$^+$(CH$_3$)$_2$),3.03~3.60(6H,m,7-CH$_2$CH$_3$ and NHCH$_2$CH$_2$NH$^+$=),5.30(2H,s,5-H$_2$),5.42(2H,dd,J=11.0 Hz,17-H$_2$),5.85(1H,d,J=15.4 Hz,CH=CH-CH$_3$),6.25~6.58(1H,br,20-OH),6.87(1H,dq,CH=CHCH$_3$),7.54(1H,s,14-H),7.73(1H,t,10-H),7.85(1H,t,11-H),8.18(1H,d,9-H),8.28(1H,d,12-H),8.39(1H,t,J=5.5 Hz,—NHCH$_2$CH$_2$NH$^+$=),10.13~10.31(1H,br,—NHCH$_2$CH$_2$NH$^+$=).

EXAMPLE 26

(Preparation of 7-ethyl-17-caproyloxycamptothecin-21-(2-dimethylamino)-ethylamide and its hydrochloride)

Using caproyl chloride(435 mg, 3.23 mmol) as an acid chloride, the reaction followed by the after-treatment was carried out with same manner as described in example 14, whereby the pale yellow crystals of title compound(226 mg, 18.7% in yield) were obtained.

m.p. 134°~137° C. (dec.)
IRν(KBr)cm$^{-1}$;
3360,2925,1725,1645,1590,1510,1455,1170.

Hydrochloride

To the suspension of free compound(160 mg) in distilled water(10 ml) the 0.1N HCl(3.4 ml) was added. An insoluble materials were filtered off and the filtrate was lyophilized to give the hydrochloride as a yellow amorphous in quantitative yield.

IRν(KBr)cm$^{-1}$;
3370,2950,2670,1720,1650,1595,1510,1455,1170.

NMR(DMSO-d$_6$)δppm;0.72~0.98(6H,m,20-CH$_2$CH$_3$ and CH$_2$(CH$_2$)$_3$CH$_3$),1.17~1.61(9H,m,7-CH$_2$CH$_3$ and CH$_2$(CH$_2$)$_3$CH$_3$),2.10~2.33(4H,m,20-CH$_2$CH$_3$ and CH$_2$(CH$_2$)$_3$CH$_3$),2.75 and 2.76(two 3H's,s,NH$^+$(CH$_3$)$_2$),3.05~3.65(6H,m,7-CH$_2$CH$_3$ and NHCH$_2$CH$_2$NH$^+$=),5.29(2H,s,5-H$_2$),5.38(2H,dd,J=11.0 Hz,17-H$_2$),6.30~6.50(1H,br,20-OH),7.56(1H,s,14-H),7.73(1H,t,10-H),7.85(1H,t,11-

H),8.17(1H,d,9-H),8.28(1H,d,12-H),8.38(1H,t,J=5.5 Hz,—NHCH$_2$CH$_2$NH+=),10.15~10.32(1H,br,—NH$\overline{\text{CH}}$$_2$CH$_2$NH+=).

EXAMPLE 27

(Preparation of 7-ethyl-17-cinnamoyloxycamptothecin-21-(2-dimethylamino)ethylamide and its hydrochloride)

Using cinnamoyl chloride(538 mg, 3.23 mmol) as an acid chloride, the reaction followed by the after-treatment was carried out with same manner as described in example 14, whereby the pale yellow crystals of title compound(447 mg, 34.9% in yield) were obtained.

m.p. 140°~143° C. (dec.)
IR$\nu$(KBr)cm$^{-1}$;
3360,2960,2930,1705,1645,1595,1510,1165.

Hydrochloride

To the suspension of free compound(200 mg) in distilled water(15 ml) the 0.1N HCl(3.7 ml) was added. An insoluble materials were filtered off and the filtrate was lyophilized to give the hydrochloride as a yellow amorphous(204 mg, 96.2% in yield).

IR$\nu$(KBr)cm$^{-1}$;
3340,2670,1700,1650,1595,1510,1165.
NMR(DMSO-d$_6$)$\delta$ppm;0.89(3H,t,J=7.3 Hz,20-CH$_2$CH$_3$),1.33(3H,t,J=7.7 Hz,7-CH$_2$CH$_3$),2.24(2H,q,20-CH$_2$CH$_3$),2.73 and 2.74(two 3H's,s,NH+=(CH$_3$)$_2$),3.03~3.60(6H,m,7-CH$_2$CH$_3$ and NHCH$_2$CH$_2$NH+=),5.32(2H,s,5-H$_2$),5.54(2H,dd,J=11.0 Hz,17-H$_2$),6.32~6.58(1H,br,20-OH),6.62(1H,d,J=16.1 Hz,CH=CHPh),7.34~7.48(3H,m,Ph),7.56(1H,s,14-H),7.64(1$\overline{\text{H}}$,d,J=16.1 Hz,CH=CHPh),7.64~7.80(3H,m,10-H and Ph),7.87(1$\overline{\text{H}}$,t,11-H),8.20(1H,d,9-H),8.30(1H,d,12-H),8.44(1H,t,J=5.5 Hz,—NHCH$_2$CH$_2$NH+=),10.15~10.38(1H,br,—NH$\overline{\text{CH}}$$_2$CH$_2$NH+=).

EXAMPLE 28

(Preparation of 7-ethyl-17-phenylacetoxycamptothecin-21-(2-dimethylamino)ethylamide and its hydrochloride)

Using phenylacetyl chloride(499 mg, 3.23 mmol) as an acid chloride, the reaction followed by the after-treatment was carried out with same manner as described in example 14, whereby the pale yellow crystals of title compound(233 mg, 18.6% in yield) were obtained.

m.p. 108°~114° C. (dec.)
IR$\nu$(KBr)cm$^{-1}$;
3370,2960,2930,1725,1645,1590,1510,1450,1140.

Hydrochloride

To the suspension of free compound(160 mg) in distilled water(10 ml) the 0.1N HCl(3.0 ml) was added. An insoluble materials were filtered off and the filtrate was lyophilized to give the hydrochloride as a yellow amorphous in quantitative yield.

IR$\nu$(KBr)cm$^{-1}$;
3300,2670,1720,1650,1595,1510,1140.
NMR(DMSO-d$_6$)$\delta$ppm;0.81(3H,t,J=7.3 Hz,20-CH$_2$CH$_3$),1.33(3H,t,J=7.7 Hz,7-CH$_2$-CH$_3$),2.17(2H,q,20-CH$_2$CH$_3$),2.74 and 2.75(two 3$\overline{\text{H}}$'s,s,NH+=(CH$_3$)$_2$),3.02~3.63(6H,m,7-CH$_2$CH$_3$ and NHCH$_2$CH$_2$NH+=),3.64(2H,s,CH$_2$Ph),5.30(2H,s,5-H$_2$),5.44(2H,dd,J=11.0 $\overline{\text{Hz}}$,17-H$_2$),6.32~6.50(1 H,br,20-OH),7.20~7.41(5H,m,Ph),7.56(1H,s,14-H),7.73(1H,t,10-H),7.85(1H,t,11-H),8.17(1H,d,9-H),8.28(1H,d,12-H),8.38(1H,t,J=5.5 Hz,—NHCH$_2$CH$_2$NH+=),10.15~10.33(1H,br,—NH$\overline{\text{CH}}$$_2$CH$_2$NH+=).

EXAMPLE 29

(Preparation of 7-ethyl-17-(4-phenylbenzoyloxycamptothecin-21-(2-dimethylamino)ethylamide and its hydrochloride)

Using 4-phenylbenzoyl chloride(700 mg, 3.23 mmol) as an acid chloride, the reaction followed by the after-treatment was carried out with same manner as described in example 14, whereby the pale yellow crystals of title compound(214 mg, 15.4% in yield) were obtained.

m.p. 197°~201° C. (dec.)
IR$\nu$(KBr)cm$^{-1}$;
3380,3310,2960,2930,1700,1655,1595,1510,1270,1100.

Hydrochloride

To the suspension of free compound(160 mg) in distilled water(10 ml) the 0.1N HCl(2.7 ml) was added. An insoluble materials were filtered off and the filtrate was lyophilized to give the hydrochloride as a yellow amorphous in quantitative yield.

IR$\nu$(KBr)cm$^{-1}$;
3360,2675,1700,1645,1595,1510,1270,1100.
NMR(DMSO-d$_6$)$\delta$ppm;0.91(3H,t,J=7.3 Hz,20-CH$_2$CH$_3$),1.33(3H,t,J=7.7 Hz,7-CH$_2$-CH$_3$),2.17~2.34(2H,m,20-CH$_2$CH$_3$),2.72 and 2.73(two 3$\overline{\text{H}}$'s,s,NH+(CH$_3$)$_2$),3.03~3.58(6H,m,7-CH$_2$CH$_3$ and NHCH$_2$CH$_2$NH+=),5.35(2H,s,5-H$_2$),5.67(2H,dd,J=11.6 Hz,17-H$_2$),6.41~6.53(1H,br,20-OH),7.36~7.56(3H,m,Arom),7.58(1H,s,14-H),7.65~7.80(3H,m,10-H and Arom),7.81(2H,d,J=8.1 Hz,Arom),7.87(1H,t,11-H),7.99(2H,d,Arom),8.20(1H,d,9-H),8.30(1H,d,12-H),8.47(1H,t,J=5.5 Hz,—NHCH$_2$CH$_2$NH+=),9.92~10.09(1H,br,—NH$\overline{\text{CH}}$$_2$CH$_2$NH+=).

EXAMPLE 30

(Preparation of 7-ethyl-17-cyclohexanecarbonyloxycamptothecin-21-(2-dimethylamino)ethylamide and its hydrochloride)

Using cyclohexanecarbonyl chloride(474 mg, 3.23 mmol) as an acid chloride, the reaction followed by the after-treatment was carried out with same manner as described in example 14, whereby the pale yellow crystals of title compound(378 mg, 30.6% in yield) were obtained.

m.p. 119°~123° C. (dec.)
IR$\nu$(KBr)cm$^{-1}$;
3360,2930,2850,1720,1650,1595,1510,1450,1245,1165.

Hydrochloride

To the suspension of free compound(200 mg) in distilled water(15 ml) the 0.1N HCl(3.8 ml) was added. An insoluble materials were filtered off and the filtrate was lyophilized to give the hydrochloride as a yellow amorphous in quantitative yield.

IR$\nu$(KBr)cm$^{-1}$;
3350,2930,2675,1715,1645,1595,1510,1450,1170.
NMR(DMSO-d$_6$)$\delta$ppm;0.85(3H,t,J=7.3 Hz,20-CH$_2$CH$_3$),1.10~1.46(8H,m,7-CH$_2$-CH$_3$ and cyclo- Hex),1.50~1.90(5H,m,cyclo-Hex),2.10~2.35(3H,m,20-CH$_2$-CH$_3$ and cyclo-Hex),2.75(6H,s,NH+(CH$_3$)$_2$),3.05~3.65(6H,m,7-CH$_2$CH$_3$ and NHCH$_2$CH$_2$NH+=),5.29(2H,s,5-H$_2$),5.36(2H,dd,J=11.0 Hz,17-H$_2$),6.41(1H,s,20-OH),7.56(1H,s,14-H),7.72(1H,t,10-H),7.85(1H,t,11-H),8.17(1H,d,9-H),8.27(1H,d,12-H),8.38(1H,t,J=5.5 Hz,—NHCH$_2$CH$_2$NH+=),10.20~10.43(1H,b-r,—NHCH$_2$CH$_2$NH+=).

EXAMPLE 31

(Preparation of 7-ethyl-17-stearoyloxycamptothecin-21-(2-dimethylamino)ethylamide and its hydrochloride)

Using stearoyl chloride(978 mg, 3.23 mmol) as an acid chloride, the reaction followed by the after-treatment was carried out with same manner as described in example 14, whereby the yellow syrup of title compound(221 mg, 14.0% in yield) was obtained.
IR$\nu$(CHCl$_3$)cm$^{-1}$;
3400,2920,2850,1725,1650,1595,1510,1455.

Hydrochloride

To the suspension of free compound(200 mg) in distilled water(20 ml) the 0.1N HCl(3.0 ml) was added. An insoluble materials were filtered off and the filtrate was lyophilized to give the hydrochloride as a yellow amorphous in quantitative yield.
IR$\nu$(KBr)cm$^{-1}$;
3340,2915,2845,2680,1720,1645,1590,1510,1460,1165.
NMR(DMSO-d$_6$)$\delta$ppm;0.85(6H,t,20-CH$_2$CH$_3$ and CH$_2$(CH$_2$)$_{15}$CH$_3$),1.08~1.59(33H,m,7-CH$_2$CH$_3$ and CH$_2$(CH$_2$)$_{15}$CH$_3$),2.12~2.30(4H,m,20-CH$_2$CH$_3$ and CH$_2$(CH$_2$)$_{15}$CH$_3$),2.76(6H,s,NH+(CH$_3$)$_2$),3.03~3.63(6H,m,7-CH$_2$CH$_3$ and NH-CH$_2$CH$_2$NH+=),5.28(2H,s,5-H$_2$),5.37(2H,dd,J=11.0 Hz,17-H$_2$),6.37(1H,s,20-OH),7.55(1H,s,14-H),7.72(1H,t,10-H),7.85(1H,t,11-H),8.17(1H,d,9-H),8.28(1H,d,12-H),8.37(1H,t,J=5.7 Hz,—NHCH$_2$CH$_2$NH+=),10.07~10.22(1H,b-r,—NHCH$_2$CH$_2$NH+=).

EXAMPLE 32

(Preparation of 7-ethyl-17-oleoyloxycamptothecin-21-(2-dimethylamino)ethylamide and its hydrochloride)

Using oleoyl chloride(972 mg, 3.23 mmol) as an acid chloride, the reaction followed by the after-treatment was carried out with same manner as described in example 14, whereby the yellow syrup of title compound(202 mg, 12.9% in yield) was obtained.
IR$\nu$(CHCl$_3$)cm$^{-1}$;
3400,2920,2850,1725,1650,1595,1510,1455.

Hydrochloride

To the suspension of free compound(163 mg) in distilled water(20 ml) the 0.1N HCl(2.5 ml) was added. An insoluble materials were filtered off and the filtrate was lyophilized to give the hydrochloride as a pale yellow amorphous in quantitative yield.
IR$\nu$(KBr)cm$^{-1}$;
3340,2920,2835,2685,1720,1645,1595,1510,1455.
NMR(DMSO-d$_6$)$\delta$ppm;0.74~0.97(6H,m,20-CH$_2$CH$_3$ and (CH$_2$)$_7$CH=CH(CH$_2$)$_7$CH$_3$),1.11~2.05(29H,m,7-CH$_2$CH$_3$ and -CH$_2$(CH$_2$)$_6$CH=CH(CH$_2$)$_7$CH$_3$),2.11~2.30(4H,m,20-CH$_2$CH$_3$ and -COCH$_2$-),2.75(6H,s,NH+(CH$_3$)$_2$),3.03~3.62(6H,m,7-CH$_2$-CH$_3$ and NHCH$_2$CH$_2$NH+=),5.20~5.50(6H,m,5-H$_2$,17-H$_2$ and —CH=CH—),6.38(1H,s,20-OH),7.55(1H,s,14-H),7.73(1H,t,10-H),7.85(1H,t,11-H),8.17(1H,d,9-H),8.28(1H,d,12-H),8.36(1H,t,J=5.5 Hz,—NHCH$_2$CH$_2$NH+=),10.03~10.21(1H,b-r,—NHCH$_2$CH$_2$NH+=).

EXAMPLE 33

(Preparation of 7-ethyl-17-(4-methoxycarbonylbenzoyloxy)camptothecin-21-(2-dimethylamino)ethylamide and its hydrochloride)

Using 4-methoxycarbonylbenzoyl chloride(542 mg, 2.73 mmol) as an acid chloride, the reaction followed by the after-treatment was carried out with same manner as described in example 14, whereby the yellow syrup of title compound(279 mg, 24.5% in yield) was obtained.
m.p. 192°~194° C. (dec.)
IR$\nu$(KBr)cm$^{-1}$;
3360,2960,2930,1720,1650,1590,1515,1270,1110,1100.

Hydrochloride

To the suspension of free compound(200 mg) in distilled water(20 ml) the 0.1N HCl(3.8 ml) was added. An insoluble materials were filtered off and the filtrate was lyophilized to give the hydrochloride as a yellow amorphous(208 mg, 98.1% in yield).
IR$\nu$(KBr)cm$^{-1}$;
3360,2675,1710,1650,1595,1510,1270,1115,1100.
NMR(DMSO-d$_6$)$\delta$ppm;0.89(3H,t,J=7.3 Hz,20-CH$_2$CH$_3$),1.33(3H,t,J=7.7 Hz,7-CH$_2$-CH$_3$),2.17~2.34(2H,m,20-CH$_2$CH$_3$),2.72 and 2.73(two 3H's,s,NH+=(CH$_3$)$_2$),3.03~3.61(6H,m,7-CH$_2$CH$_3$ and NHCH$_2$CH$_2$NH+=),3.88(3H,s,CO$_2$CH$_3$),5.33(2H,s,5-H$_2$),5.70(2H,dd,J=11.0 Hz,17-H$_2$),6.32~6.64(1H,br,20-OH),7.58(1H,s,14-H),7.74(1H,t,10-H),7.86(1H,t,11-H),8.03 and 8.07(two 2H's,s,C$_6$H$_4$-CO$_2$CH$_3$),8.19(1H,d,9-H),8.29(1H,d,12-H),8.48(1H,t,J=5.5 Hz,—NHCH$_2$CH$_2$NH+=),10.09~10.25(1H,b-r,—NHCH$_2$CH$_2$NH+=).

EXAMPLE 34

(Preparation of 7-ethyl-17-ethylsuccinyloxycamptothecin-21-(2-dimethylamino)ethylamide and its hydrochloride)

Using ethylsuccinyl chloride(449 mg, 2.73 mmol) as an acid chloride, the reaction followed by the after-treatment was carried out with same manner as described in example 14, whereby the yellow syrup of title compound(253 mg, 23.5% in yield) was obtained.
m.p. 120°~121° C. (dec.)
IR$\nu$(KBr)cm$^{-1}$;
3370,2970,2930,1730,1645,1590,1155.

Hydrochloride

To the suspension of free compound(200 mg) in distilled water(20 ml) the 0.1N HCl(4.1 ml) was added. An insoluble materials were filtered off and the filtrate was lyophilized to give the hydrochloride as a yellow amorphous(200 mg, 94.3% in yield).
IR$\nu$(KBr)cm$^{-1}$;
3370,2670,2930,2680,1725,1645,1595,1515,1155.
NMR(DMSO-d$_6$)$\delta$ppm;0.86(3H,t,J=7.3 Hz,20-CH$_2$CH$_3$),1.19(3H,t,J=7.3 Hz,—CO$_2$-CH$_2$CH$_3$),1.33(3H,t,J=7.3 Hz,7-

CH$_2$CH$_3$),2.21(2H,q,20-CH$_2$CH$_3$),2.54(4H,br,CH$_2$CH$_2$CO$_2$Et),2.75 and 2.77(two 3H's,s,NH+(CH$_3$)$_2$),3.05~3.72(6H,m,7-CH$_2$CH$_3$ and NHCH$_2$CH$_2$NH+=),4.07(2H,q,CO$_2$CH$_2$CH$_3$),5.29(2-H,s,5-H$_2$),5.42(2H,dd,J=10.6 Hz,17-H$_2$),6.22~6.62(1H,br,20-OH),7.55(1H,s,14-H),7.72(1H,t,10-H),7.85(1H,t,11-H),8.18(1H,d,9-H),8.27(1H,d,12-H),8.381H,t,J=5.5 Hz,—NHCH$_2$CH$_2$NH+=),10.26~10.47(1H,br,—NHCH$_2$NH+=).

EXAMPLE 35

(Preparation of 7-ethyl-17-linoleoyloxycamptothecin-21-(2-dimethylamino)ethylamide and its hydrochloride)

Using linoleoyl chloride(816 mg, 2.73 mmol) as an acid chloride, the reaction followed by the after-treatment was carried out with same manner as described in example 14, whereby the yellow syrup of title compound(280 mg, 21.2% in yield) was obtained.
IR$\nu$(CHCl$_3$)cm$^{-1}$;
3400,2920,2850,1725,1650,1595,1510,1455.

Hydrochloride

To the suspension of free compound(250 mg) in distilled water(25 ml) the 0.1N HCl(4.1 ml) was added. An insoluble materials were filtered off and the filtrate was lyophilized to give the hydrochloride as a yellow amorphous in quantitative yield.
IR$\nu$(KBr)cm$^{-1}$;
3280,2920,2850,2680,1720,1650,1600,1510,1455,1170.
NMR(DMSO-d$_6$)$\delta$ppm;0.73~0.95(6H,m,20-CH$_2$CH$_3$ and —(CH$_2$)$_7$CH=CHCH$_2$CH=CH-(CH$_2$)$_4$CH$_3$),1.06~1.62(23H,m,7-CH$_2$CH$_3$ and -CH$_2$(CH$_2$)$_6$CH=CHCH$_2$CH=CH-(CH$_2$)$_4$CH$_3$),1.92~2.06(2H,m,=CHCH$_2$CH=),2.11~2.30(4H,m,20-CH$_2$CH$_3$ and —COCH$_2$—),2.75(6H,s,NH+(CH$_3$)$_2$),3.00~3.63(6H,m,7-CH$_2$CH$_3$ and NHCH$_2$CH$_2$NH+=),5.18~5.50(8H,m,5-H$_2$,17-H$_2$ and —CH=CH-x2),6.38(1H,s,20-OH),7.55(1H,s,14-H),7.73(1H,t,10-H),7.85(1H,t,11-H),8.17(1H,d,9-H),8.28(1H,d,12-H),8.35(1H,t,J=5.8 Hz,—NHCH$_2$CH$_2$NH+=),9.95~10.50(1H,br,—NHCH$_2$CH$_2$-NH+=).

EXAMPLE 36

(Preparation of 7-ethyl-17-(4-chlorobutyryloxy)camptothecin-21-(2-dimethylamino)ethylamide and its hydrochloride)

Using 4-chlorobutyryl chloride(385 mg, 2.73 mmol) as an acid chloride, the reaction followed by the after-treatment was carried out with same manner as described in example 14, whereby the yellow crystals of title compound(227 mg, 22.0% in yield) were obtained.
m.p. ~199° C. (dec.)
IR$\nu$(KBr)cm$^{-1}$;
3370,2960,2930,1725,1645,1590,1510,1455,1210,1185,1140.
NMR(CDCl$_3$)$\delta$ppm;1.09(3H,t,J=7.3 Hz,20-CH$_2$CH$_3$),1.35(3H,t,J=7.7 Hz,7-CH$_2$-CH$_3$),2.03~2.15(2H,m,CH$_2$CH$_2$CH$_2$Cl),2.22(6H,s,—N(CH$_3$)$_2$),2.25~2.57(6H,m,—CH$_2$CH$_2$N=,CH$_2$CH$_2$CH$_2$Cl and 20-CH$_2$CH$_3$),3.01~3.48(4H,m,7-CH$_2$CH$_3$ and NHCH$_2$CH$_2$N=),3.61(2H,t,J=6.6 Hz,CH$_2$CH$_2$CH$_2$Cl),5.11(2H,dd,J=18.7 Hz,5-H$_2$),5.13(1H,s,20-OH),5.53(2H,dd,J=11.7 Hz,17-H$_2$),7.35(1H,t,—NHCH$_2$CH$_2$N=),7.52~7.58(2H,m,10-H and 14-H),7.73(1H,m,11-H),7.93(1H,d,9-H),8.12(1H,d,12-H).

Hydrochloride

To the suspension of free compound(150 mg) in distilled water(10 ml) the 0.1N HCl(3.2 ml) was added. An insoluble materials were filtered off and the filtrate was lyophilized to give the hydrochloride as a yellow amorphous in quantitative yield.
IR$\nu$(KBr)cm$^{-1}$;
3280,2970,2930,2675,1720,1645,1595,1510,1450.
NMR(DMSO-d$_6$)$\delta$ppm;0.86(3H,t,J=7.3 Hz,20-CH$_2$CH$_3$),1.33(3H,t,7-CH$_2$CH$_3$),1.93~2.05(2H,m,CH$_2$CH$_2$CH$_2$Cl),2.21(2H,q,20-CH$_2$CH$_3$),2.43(2H,t,J=7.3 Hz,CH$_2$CH$_2$CH$_2$Cl),2.75 and 2.76(two 3H's,s,NH+(CH$_3$)$_2$),3.04~3.62(6H,m,7-CH$_2$CH$_3$ and NHCH$_2$CH$_2$NH+=),3.68(2H,t,J=6.6 Hz,CH$_2$CH$_2$CH$_2$Cl),5.30(2H,s,5-H$_2$),5.41(2H,dd,J=10.6 Hz,17-H$_2$),6.28~6.53(1H,br,20-OH),7.54(1H,s,14-H),7.73(1H,t,10-H),7.85(1H,t,11-H),8.17(1H,d,9-H),8.28(1H,d,12-H),8.39(1H,t,J=5.5 Hz,—NHCH$_2$CH$_2$NH+=),10.11~10.27(1H,br,—NHCH$_2$CH$_2$NH+=).

EXAMPLE 37

(Preparation of 7-ethyl-17-((S)-(−)-N-(trifluoroacetyl)prolyloxy)camptothecin-21-(2-dimethylamino)ethylamide and its hydrochloride)

Using (S)-(−)-N-(trifluoroacetyl)prolyl chloride(0.1M solution in dichloromethane, 18.2 ml) as an acid chloride, the reaction followed by the after-treatment was carried out with same manner as described in example 14, whereby the yellow crystals of title compound(200 mg, 16.8% in yield) were obtained.
m.p. ~152° C. (dec.)
IR$\nu$(KBr)cm$^{-1}$;
3370,2960,2930,1740,1690,1650,1595,1510,1450,1235,1200,1140.
NMR(CDCl$_3$)$\delta$ppm;1.06(3H,t,J=7.3 Hz,20-CH$_2$CH$_3$),1.38(3H,t,J=7.7 Hz,7-CH$_2$-CH$_3$),1.94~2.53(14H,m,—N(CH$_3$)$_2$,—CH$_2$CH$_2$N=,Proline, and 20-CH$_2$CH$_3$),3.17(2H,q,7-CH$_2$CH$_3$),3.25~3.50(2H,m,—NHCH$_2$CH$_2$N=),3.65~3.95(2H,m,Proline),4.37(1H,br,20-OH),4.42~4.53(1H,m,Proline),5.19(2H,dd,J=18.7 Hz,5-H$_2$),5.68(1H,dd,J=11.0 Hz,17-H$_2$),7.46(1H,t,J=5.0 Hz,—NHCH$_2$CH$_2$N=),7.64(1H,t,10-H),7.74(1H,s,14-H),7.78(1H,t,11-H),8.08(1H,d,9-H),8.21(1H,d,12-H).

Hydrochloride

To the suspension of free compound(150 mg) in distilled water(10 ml) the 0.1N HCl(2.7 ml) was added. An insoluble materials were filtered off and the filtrate was lyophilized to give the hydrochloride as a yellow amorphous in quantitative yield.
IR$\nu$(KBr)cm$^{-1}$;
3370,2965,2675,1735,1685,1650,1595,1510,1455,1230,1205,1145.
NMR(DMSO-d$_6$)$\delta$ppm;0.84(3H,t,J=7.3 Hz,20-CH$_2$CH$_3$),1.33(3H,t,J=7.7 Hz,7-CH$_2$CH$_3$),1.80~2.38(6H,m,Proline and 20-CH$_2$CH$_3$),2.75 and 2.76(two 3H's,s,NH+(CH$_3$)$_2$),3.01~3.82(8H,m,7-CH$_2$CH$_3$,NHCH$_2$CH$_2$N≡, and Proline),4.43~4.62(1H,m,Proline),5.29(2H,s,5-H$_2$),5.45(2H,dd,J=11.0 Hz,17-H$_2$),6.30~6.70(1H,br,20-OH),7.58(1H,s,14-H),7.73(1H,t,10-H),7.85(1H,t,11-H),8.18(1H,d,9-H),8.28(1H,d,12-H),8.40(1H,t,J=5.5 Hz,—NHCH$_2$CH$_2$NH+≡),10.20~10.44(1H,br,—NHCH$_2$CH$_2$NH+≡).

EXAMPLE 38

(Preparation of 7-ethyl-17-(4-ethylbenzoyloxy)camptothecin-21-(2-dimethylamino)ethylamide and its hydrochloride)

Using 4-ethylbenzoyl chloride(460 mg, 2.73 mmol) as an acid chloride, the reaction followed by the after-treatment was carried out with same manner as described in example 14, whereby the yellow crystals of title compound(763 mg, 70.4% in yield) were obtained.

m.p. 140°~144° C. (dec.)

IR$\nu$(KBr)cm$^{-1}$;
3380,2960,2930,1710,1650,1605,1510,1455,1270,1105.

Hydrochloride

To the suspension of free compound(300 mg) in distilled water(20 ml) the 0.1N HCl(5.5 ml) was added. An insoluble materials were filtered off and the filtrate was lyophilized to give the hydrochloride as a yellow amorphous(295 mg, 92.6% in yield).

IR$\nu$(KBr)cm$^{-1}$;
3360,2670,1700,1645,1595,1510,1275,1105.

NMR(DMSO-d$_6$)$\delta$ppm;0.88(3H,t,J=7.3 Hz,20-CH$_2$CH$_3$),1.18(3H,t,J=7.7 Hz,C$_6$H$_4$-CH$_2$CH$_3$),1.32(3H,t,J=7.7 Hz,7-CH$_2$CH$_3$),2.16~2.35(2H,m,20-CH$_2$CH$_3$),2.66(2H,q,C$_6$H$_4$CH$_2$CH$_3$),2.70 and 2.72(two 3H's,s,NH+(CH$_3$)$_2$),3.00~3.59(6H,m,7-CH$_2$CH$_3$ and NHCH$_2$CH$_2$NH+≡),5.33(2H,s,5-H$_2$),5.62(2H,dd,J=11.0 Hz,17-H$_2$),6.36~6.57(1H,br,20-OH),7.33(2H,d,J=8.1 Hz,Arom),7.58(1H,s,14-H),7.73(1H,t,10-H),7.82(2H,d,Arom),7.88(1H,t,11-H),8.19(1H,d,9-H),8.29(1H,d,12-H),8.44(1H,t,J=5.5 Hz,—NHCH$_2$CH$_2$NH+≡),10.02~10.22(1H,br,—NHCH$_2$CH$_2$NH+≡).

EXAMPLE 39

(Preparation of 7-ethyl-17-(3-methylthiopropionyloxy)camptothecin-21-(2-dimethylamino)ethylamide and its hydrochloride)

Using 3-methylthiopropionyl chloride(378 mg, 2.75 mmol) as an acid chloride, the reaction followed by the after-treatment was carried out with same manner as described in example 14, whereby the yellow crystals of title compound(766 mg, 74.4% in yield) were obtained.

m.p. 96°~103° C. (dec.)

IR$\nu$(KBr)cm$^{-1}$;
3350,2960,2930,1730,1645,1590,1510,1455,1250,1215,1185,1140.

Hydrochloride

To the suspension of free compound(300 mg) in distilled water(20 ml) the 0.1N HCl(5.8 ml) was added. An insoluble materials were filtered off and the filtrate was lyophilized to give the hydrochloride as a yellow amorphous(314 mg, 98.4% in yield).

IR$\nu$(KBr)cm$^{-1}$; 3355,2675,1725,1645,1595,1515.

NMR(DMSO-d$_6$)$\delta$ppm;0.86(3H,t,J=7.3 Hz,20-CH$_2$CH$_3$),1.33(3H,t,7-CH$_2$CH$_3$),2.07(3H,s,SCH$_3$),2.22(2H,q,J=7.0 Hz,20-CH$_2$CH$_3$),2.57 and 2.69(two 3H's,t,COCH$_2$CH$_2$SCH$_3$),2.75 and 2.76(two 3H's,s,NH+(CH$_3$)$_2$),3.03~3.68(6H,m,7-CH$_2$CH$_3$ and NHCH$_2$CH$_2$NH+≡),5.29(2H,s,5-H$_2$),5.42(2H,dd,J=11.0 Hz,17-H$_2$),6.25~6.58(1H,br,20-OH),7.55(1H,s,14-H),7.72(1H,t,10-H),7.85(1H,t,11-H),8.17(1H,d,9-H),8.27(1H,d,12-H),8.39(1H,t,J=5.5 Hz,—NHCH$_2$CH$_2$NH+≡),10.18~10.44(1H,br,—NHCH$_2$CH$_2$NH+≡).

EXAMPLE 40

(Preparation of 7-ethyl-17-(pivaloyloxy)camptothecin-21-(2-dimethylamino)ethylamide and its hydrochloride)

Using pivaloyl chloride(329 mg, 2.75 mmol) as an acid chloride, the reaction followed by the after-treatment was carried out with same manner as described in example 14, whereby the yellow crystals of title compound(362 mg, 36.3% in yield) were obtained.

m.p. 202°~204° C. (dec.)

IR$\nu$(KBr)cm$^{-1}$;
3400,3250,2960,1715,1670,1645,1585,1515,1455,1280,1160.

Hydrochloride

To the suspension of free compound(200 mg) in distilled water(20 ml) the 0.1N HCl(4.0 ml) was added. An insoluble materials were filtered off and the filtrate was lyophilized to give the hydrochloride as a yellow amorphous(200 mg, 93.9% in yield).

IR$\nu$(KBr)cm$^{-1}$;
3360,2960,2685,1710,1645,1595,1510,1280,1155.

NMR(DMSO-d$_6$)$\delta$ppm;0.85(3H,t,J=7.3 Hz,20-CH$_2$CH$_3$),1.14(9H,s,C(CH$_3$)$_3$),1.33(3H,t,7-CH$_2$CH$_3$),2.10(2H,m,20-CH$_2$CH$_3$),2.75 and 2.76(two 3H's,s,NH+(CH$_3$)$_2$),3.05~3.67(6H,m,7-CH$_2$CH$_3$ and NHCH$_2$CH$_2$NH+≡),5.29(2H,dd,J=18.7 Hz,5-H$_2$),5.35(2H,dd,J=11.0 Hz,17-H$_2$),6.27~6.56(1H,br,20-OH),7.60(1H,s,14-H),7.72(1H,t,10-H),7.84(1H,t,11-H),8.17(1H,d,9-H),8.27(1H,d,12-H),8.39(1H,t,J=5.5 Hz,—NHCH$_2$CH$_2$NH+≡),10.18~10.40(1H,br,—NHCH$_2$CH$_2$-NH+≡).

EXAMPLE 41

(Preparation of 7-ethyl-17-phenoxyacetoxycamptothecin-21-(2-dimethylamino)ethylamide)

Using phenoxyacetyl chloride(551 mg, 3.23 mmol) as an acid chloride, the reaction followed by the after-treatment was carried out with same manner as described in example 14, whereby the yellow syrup of title compound(161 mg) was obtained, which was crystallized from CHCl$_3$-n-hexane to give yellow crystals(62 mg, 4.8% in yield).

m.p. 112°~117° C. (dec.)

IR$\nu$(KBr)cm$^{-1}$; 3360,2960,2920,1750,1650,1595.

NMR(CDCl$_3$)$\delta$ppm;1.07(3H,t,J=7.3 Hz,20-CH$_2$CH$_3$),1.35(3H,t,J=7.7 Hz,7-CH$_2$CH$_3$),2.19(6H,s,N(CH$_3$)$_2$),2.22~2.57(4H,m,—CH$_2$CH$_2$N≡ and 20-CH$_2$CH$_3$),3.10(2H,q,7-CH$_2$CH$_3$),3.24~3.46(2H,m,NHCH$_2$CH$_2$N≡),4.64(2H,s,COCH$_2$OPh),4.93~5.28(1H,br,20-OH),5.09(2H,dd,J=18.7 Hz,5-H$_2$),5.65(1H,dd,J=11.4 Hz,17-H$_2$),6.82~7.03(3H,m,OPh),7.21~7.31(2H,m,OPh),7.36(1H,t,J=5.5

Hz,NH$\underline{CH_2}$CH$_2$N≡),7.52(1H,t,10-H),7.55(1H,s,14-H),7.72(1H,t,11-H),7.88(1H,d,9-H),8.09(1H,d,12-H).

EXAMPLE 42

(Preparation of 7-ethyl-17-(3-ethoxypropionyloxy)camptothecin-21-(2-dimethylamino)ethylamide)

To the ice-cooling solution of 3-ethoxypropionic acid(323 mg, 2.73 mmol) in dichloromethane, N,N'-dicyclohexylcarbodiimide(DCC, 846 mg, 4.10 mmol) was added and the reaction mixture was stirred for 0.5 hour. After adding the solution of 7-ethyl-17-hydroxycamptothecin-21-(2-dimethylamino)ethylamide(1.00 g, 2.15 mmol) in dichloromethane(10 ml) and 4-N,N-dimethylaminopyridine(100 mg, 0.82 mmol), the reaction mixture was stirred for an hour under ice-cooling and then for an hour at room temperature. The reaction mixture was evaporated to dryness under reduced pressure, and the residual materials were purified through silica gel column chromatography with CHCl$_3$-MeOH as an eluent and crystallized from CHCl$_3$-n-hexane to give yellow crystals of title compound(50 mg, 4.9% in yield).

m.p. 119°~123° C. (dec.)

IR$\nu$(KBr)cm$^{-1}$;
3370,2960,2930,2860,1730,1645,1590,1515,1455,1180.

NMR(CDCl$_3$)δppm;1.07(3H,t,J=7.3 Hz,20-CH$_2$$\underline{CH_3}$),1.17(3H,t,J=7.0 Hz,OCH$_2$$\underline{CH_3}$),1.36(3H,t,J=7.7 Hz,7-$\overline{CH_2}$$\underline{CH_3}$),2.23(6H,s,—N(CH$_3$)$_2$),2.24~2.53(4H,m,—CH$_2$$\underline{CH_2}$N≡and 20-C$\underline{H_2}$CH$_3$),2.61(2H,t,J=6.2 Hz,—COC$\underline{H_2}$CH$_2$O),3.02~3.58(6H,m,7-$\underline{CH_2}$CH$_3$,—N$\underline{H}$CH$_2$CH$_2$N≡ and OC$\underline{H_2}$CH$_3$),3.62~3.80(2H,m,—COCH$_2$C$\underline{H_2}$O),4.80~5.10(1H,br,20-OH),5.13(2H,$\overline{dd}$,J=18.7 Hz,5-H$_2$),5.55(2H,dd,J=11.4 Hz,17-H$_2$),7.38(1H,t,J=5.5 Hz,—N$\underline{H}$CH$_2$CH$_2$N≡),7.56(1H,t,10-H),7.60(1H,s,14-H),7.74($\overline{1H}$,t,11-H),7.96(1H,d,9-H),8.14(1H,d,12-H).

EXAMPLE 43

(Preparation of 7-ethyl-17-(N-tert-butoxycarbonyl-L-alanyloxy)camptothecin-21-(2-dimethylamino)ethylamide)

To the salt-ice-cooling solution of tert-butoxycarbonyl-L-alanine (517 mg, 2.73 mmol) in THF(15 ml), triethylamine(0.38 ml, 2.73 mmol) and iso-butyl chloroformate(373 mg, 2.73 mmol) were added and the reaction mixture was stirred for 5 minutes. After adding the solution of 7-ethyl-17-hydroxycamptothecin-21-(2-dimethylamino)ethylamide(1.00 g, 2.15 mmol) in THF(15 ml) and 4-N,N-dimethylaminopyridine(100 mg, 0.82 mmol), the reaction mixture was stirred for an hour under ice-cooling and then for 3 hours at room temperature. The reaction mixture was evaporated to dryness under reduced pressure, and the residual materials were dissolved in CHCl$_3$ and washed with a saturated aqueous solution of NaHCO$_3$ and with a saturated aqueous solution of NaCl. The organic phase was separated, dried with anhydrous MgSO$_4$, and then evaporated to dryness under reduced pressure. The residual materials were purified through silica gel column chromatography with CHCl$_3$-MeOH as an eluent and crystallized from CHCl$_3$-n-hexane to give pale yellow crystals of title compound(91 mg, 7.9% in yield).

m.p. ~130° C.(dec.)

IR$\nu$(KBr)cm$^{-1}$;
3340,2970,2930,1735,1705,1650,1595,1510,1450,1160.

NMR(CDCl$_3$)δppm;1.07(3H,t,J=7.3 Hz,20-CH$_3$$\underline{CH_3}$),1.28~1.48(15H,m,7-CH$_2$-$\underline{CH_3}$,—CH($\underline{CH_3}$)— and —C(CH$_3$)$_3$),2.20~2.53(4H,m,—CH$_2$$\underline{CH_2}$N≡ and 20-C$\underline{H_2}$CH$_3$),2.25(6H,s,—N(CH$_3$)$_2$),3-.15(2H,q,7-$\underline{CH_2}$CH$_3$),3.27~3.50(2H,m,—NHCH$_2$CH$_2$-N≡),4.13~4.30(1H,m,COC$\underline{H}$(CH$_3$)NH-CO),4.63~5.04(1H,br,20-O$\underline{H}$),5.17(2H,dd,J=18.7 Hz,5-H$_2$),5.28(1H,d,J=6.6 Hz,COCH(CH$_3$)N$\underline{H}$$\underline{CO}$),5.62(2H,dd,J=11.0 Hz,17-H$_2$),7.46(1H,br-t,—N$\underline{H}$CH$_2$CH$_2$N≡),7.61(1H,t,10-H),7.68(1H,s,14-H),7.76(1H,t,11-H),8.04(1H,d,9-H),8.18(1H,d,12-H).

EXAMPLE 44

(Preparation of 7-ethyl-17-nicotinyloxycamptothecin-21-(2-dimethylamino)ethylamide and its dihydrochloride To the ice-cooling DMF solution(10 ml) of 7-ethyl-17-hydroxycamptothecin-21-(2-dimethylamino)ethylamide(1.00 g, 2.15 mmol), the DMF solution (10 ml) of nicotinyl chloride hydrochloride(575 mg, 3.23 mmol) was added in the presence of 4-N,N-dimethylaminopyridine(100 mg, 0.82 mmol). The reaction mixture was stirred for an hour under ice-cooling and for 0.5 hours at room temperature. Then the reaction mixture was evaporated to dryness under reduced pressure, and the residual materials were dissolved in CHCl$_3$ and washed with a saturated aqueous solution of NaHCO$_3$ and with a saturated aqueous solution of NaCl. The organic phase was separated, dried with anhydrous Na$_2$SO$_4$, then evaporated to dryness under reduced pressure. The resulting materials were purified through silica gel column chromatography with CHCl$_3$-MeOH as an eluent and crystallized from CHCl$_3$-n-hexane to give pale yellow crystals of the title compound (157 mg, 12.8% in yield).

m.p. ~162° C.(dec.)

IR$\nu$(KBr)cm$^{-1}$;
3360,2970,2930,1715,1645,1590,1510,1275,1110.

Dihydrochloride

To the suspension of free compound(120 mg) in distilled water(20 ml) the 0.1N HCl(4.6 ml) was added. An insoluble materials were filtered off and the filtrate was lyophilized to give the dihydrochloride as a yellow amorphous(126 mg, 93.3% in yield).

IR$\nu$(KBr)cm$^{-1}$;
3375,2680,1730,1645,1590,1520,1460,1290,1130.

NMR(DMSO-d$_6$)δppm;0.89(3H,t,J=7.3 Hz,20-CH$_2$$\underline{CH_3}$),1.32(3H,t,J=7.7 Hz,7-CH$_2$-$\underline{CH_3}$),2.13~2.38(2H,m,20-C$\underline{H_2}$CH$_3$),2.72 and 2.73(two 3H's,s,NH+(CH$_3$)$_2$),3.02~3.64(6H,m,7-$\underline{CH_2}$CH$_3$ and NH$\underline{CH_2}$CH$_2$NH+≡),5.32(2H,s,5-H$_2$),5.73(2H,dd,J=11.0 Hz,17-H$_2$),6.30~6.75(1H,br,20-OH),7.58(1H,s,14-H),7.60~7.78(2H,m,10-H and Py),7.86(1H,t,11-H),8.20(1H,d,9-H),8.24~8.37(2H,m,12-H and Py),8.49(1H,t,J=5.5 Hz,—N$\underline{H}$CH$_2$CH$_2$NH+≡),8.84(1H,dd,J=1.8 and 5.1 Hz,Py),9.06(1H,d,J=1.5 Hz,Py),10.22~10.42(1H,br,—NHCH$_2$CH$_2$N$\underline{H}$+≡).

EXAMPLE 45

(Preparation of
7-ethyl-17-iso-nicotinyloxycamptothecin-21-(2-dimethylamino)ethylamide and its dihydrochloride)

Using iso-nicotinyl chloride hydrochloride(575 mg, 3.23 mmol) as an acid chloride, the reaction followed by the after-treatment was carried out with same manner as described in example 44, whereby the yellow crystals of title compound(445 mg, 36.3% yield) were obtained.

m.p. 168°~171° C.(dec.)

IR$\nu$(KBr)cm$^{-1}$;
3350,2960,2930,1720,1645,1595,1510,1275,1120.

Dihydrochloride

To the suspension of free compound(200 mg) in distilled water(15 ml) the 0.1N HCl(7.7 ml) was added. An insoluble materials were filtered off and the filtrate was lyophilized to give the dihydrochloride as a yellow amorphous in quantitative yield.

IR$\nu$(KBr)cm$^{-1}$;
3360,2675,1725,1645,1590,1510,1280,1120.

NMR(DMSO-d$_6$)$\delta$ppm;0.89(3H,t,J=7.3 Hz,20-CH$_2$CH$_3$),1.32(3H,t,J=7.3 Hz,7-CH$_2$-CH$_3$),2.14~2.38(2H,m,20-CH$_2$CH$_3$),2.72 and 2.73(two 3H's,s,NH$^+$(CH$_3$)$_2$),3.02~3.63(6H,m,7-CH$_2$CH$_3$ and NHCH$_2$CH$_2$NH$^+$=),5.33(2H,s,5-H$_2$),5.77(2H,dd,J=11.0 Hz,17-H$_2$),6.26~6.80(1H,br,20-OH),7.58(1H,s,14-H),7.74(1H,t,10-H),7.87(1H,t,11-H),7.91(2H,d,J=5.1 Hz,Py),8.21(1H,d,9-H),8.30(2H,d,12-H),8.51(1H,t,J=5.5 Hz,—NHCH$_2$CH$_2$NH$^+$=),8.87(2H,d,Py),10.29~10.47(1H,br,—NHCH$_2$CH$_2$NH$^+$=).

EXAMPLE 46

(Preparation of
7-ethyl-17-picolinoyloxycamptothecin-21-(2-dimethylamino)ethylamide)

Using picolinoyl chloride hydrochloride(575 mg, 3.23 mmol) as an acid chloride, the reaction followed by the after-treatment was carried out with same manner as described in example 44, whereby the yellow crystals of title compound(23 mg, 1.9% in yield) were obtained.

m.p. ~3/8° C.(dec.)

IR$\nu$(KBr)cm$^{-1}$;
3370,2960,2930,1715,1650,1595,1510,1455,1305,1285,1245,1130.

NMR(CDCl$_3$)$\delta$ppm;1.06(3H,t,J=7.3 Hz,20-CH$_2$CH$_3$),1.38(3H,t,J=7.3 Hz,7-CH$_2$-CH$_3$),2.15~2.55(4H,m,20-CH$_2$CH$_3$ and NHCH$_2$CH$_2$NH$^+$=),2.23(3H,s,NH(CH$_3$)$_2$),3.16(2H,q,-7-CH$_2$CH$_3$),3.26~3.50(2H,m,NHCH$_2$CH$_2$NH$^+$=),5.0-7~5.53(1H,br,20-OH),5.19(2H,s,5-H$_2$),5.87(2H,dd,J=11.4 Hz,17-H$_2$),7.50(1H,br,—NH—),7.62(1H,t,10-H),7.65(1H,s,14-H),7.74~7.85(2H,m,11-H and Py),8.06(1H,d,9-H),8.13~8.23(2H,m,12H and Py),8.65~8.70(1H,m,Py).

What is claimed is:

1. Camptothecin derivatives of the formula:

wherein

X is a lower alkyl group, and R is a hydrogen atom or the grouping -COY where Y is a linear or branched unsubstituted C$_1$-C$_{18}$ alkyl group; a lower alkyl group substituted by a halogen atom or a lower alkylthio, amino, acylamino, hydroxyl, lower alkoxy, aryloxy or lower alkoxycarbonyl group; a C$_3$-C$_{19}$ alkenyl, C$_3$-C$_{19}$ alkynyl or C$_3$-C$_8$ cycloalkyl group; a C$_3$-C$_8$ cycloalkyl group substituted by an acylamino-lower alkyl group; an N-acylpyrrolidyl group; a phenyl group; a phenyl group substituted by a halogen atom or a trifluoromethyl, nitro, amino, lower alkoxycarbonyl, lower alkyl, phenyl or lower alkoxy; a cinnamyl group; a benzyl group; a naphthyl group; a pyridyl group; a furyl group; or a thienyl group, and their physiologically acceptable acid addition salts formed at the amino group and quaternary ammonium salts.

* * * * *